US010301598B2

United States Patent
Cho et al.

(10) Patent No.: US 10,301,598 B2
(45) Date of Patent: May 28, 2019

(54) LOW-MOLECULAR-COMPOUND FOR IMPROVING PRODUCTION, MAINTENANCE AND PROLIFERATION OF PLURIPOTENT STEM CELLS, COMPOSITION COMPRISING THE SAME, AND CULTURE METHOD

(71) Applicant: Korea Research Institute of Bioscience and Biotechnology, Daejeon (KR)

(72) Inventors: Yee Sook Cho, Daejeon (KR); Kyeong Lee, Seoul (KR); Jung Woon Lee, Daejeon (KR)

(73) Assignee: KOREA RESEARCH INSTITUTE OF BIOSCIENCE AND BIOTECHNOLOGY (KR)

( * ) Notice: Subject to any disclaimer, the term of this patent is extended or adjusted under 35 U.S.C. 154(b) by 22 days.

(21) Appl. No.: 15/411,642

(22) Filed: Jan. 20, 2017

(65) Prior Publication Data

US 2017/0159023 A1    Jun. 8, 2017

Related U.S. Application Data

(62) Division of application No. 14/358,672, filed as application No. PCT/KR2012/009420 on Nov. 8, 2012, now Pat. No. 9,587,225.

(30) Foreign Application Priority Data

May 29, 2012  (KR) .................. 10-2012-0056881
May 30, 2012  (KR) .................. 10-2012-0057803

(51) Int. Cl.
```
C12N 5/00       (2006.01)
C12N 5/074      (2010.01)
C07D 209/20     (2006.01)
C07D 209/18     (2006.01)
C07D 209/24     (2006.01)
C07D 405/12     (2006.01)
C12N 5/0735     (2010.01)
```

(52) U.S. Cl.
CPC ......... *C12N 5/0696* (2013.01); *C07D 209/18* (2013.01); *C07D 209/20* (2013.01); *C07D 209/24* (2013.01); *C07D 405/12* (2013.01); *C12N 5/0606* (2013.01); *C12N 2500/02* (2013.01); *C12N 2500/30* (2013.01); *C12N 2501/115* (2013.01); *C12N 2501/602* (2013.01); *C12N 2501/603* (2013.01); *C12N 2501/604* (2013.01); *C12N 2501/606* (2013.01); *C12N 2501/999* (2013.01); *C12N 2506/02* (2013.01); *C12N 2506/09* (2013.01)

(58) Field of Classification Search
CPC ............................ C12N 5/0696; C07D 209/20
See application file for complete search history.

(56) References Cited

FOREIGN PATENT DOCUMENTS

| KR | 10-0842351 B1  | 6/2008  |
|----|----------------|---------|
| WO | 2012/136476 A1 | 10/2012 |
| WO | 2013/180350 A1 | 12/2013 |

OTHER PUBLICATIONS

Lee et al. Angew. Chem. Int. Ed. 51:12509-12513, Nov. 4, 2012. With supplementary materials pp. 1-17 (Year: 2012).*
Han et al. (2011) "Induced Pluripotent Stem Cells: Emerging Techniques for Nuclear Reprogramming," Antioxidants & Redox Signaling. 15(7):1799-1820.
Hochedlinger et al. (2006) "Nuclear Reprogramming and Pluripotency," Nature. 441:1061-1067.
Huangfu et al. (2008) "Induction of pluripotent stem cells from primary human fibroblasts with only Oct4 and Sox2," Nature Biotechnology. 26(11):1269-1275.
Huangfu et al. (2008) "Induction of Pluripotent Stem Cells by Defined Factors is Greatly Improved by Small-molecule Compounds," Nature Biotechnology. 26:795-797.
Park et al. (2008) "Reprogramming of Human Somatic Cells to Pluripotency with Defined Factors," Nature. 451:141-146.
Shi et al. (2008) "Induction of Pluripotent Stem Cells from Mouse Embryonic Fibroblasts by Oct4 and Klf4 with Small-Molecule Compounds," Cell Stem Cell. 3(5):568-574.
Takahashi et al. (2007) "Induction of Pluripotent Stem Cells from Adult Human Fibroblasts by Defined Factors," Cell. 131:861-872.
Takahashi et al. (2006) "Induction of Pluripotent Stem Cells from Mouse Embryonic and Adult Fibroblast Cultures by Defined Factors," Cell. 126:663-676.
International Search Report corresponding to International Patent Application No. PCT/KR2012/009420, dated Mar. 15, 2013—English translation provieded only.

* cited by examiner

*Primary Examiner* — Marcia S Noble
(74) *Attorney, Agent, or Firm* — Lathrop Gage LLP; Andrew T. Wilkins

(57) ABSTRACT

Provided herein are novel indoleacrylic acid-based compounds, and pharmaceutically acceptable salts thereof, useful for the production, maintenance and proliferation of pluripotent stem cells. Also provided are cell culture compositions comprising these compounds, and methods of using these compounds in the production and maintenance of pluripotent stem cells.

8 Claims, 30 Drawing Sheets
Specification includes a Sequence Listing.

FIG. 4A
FIG. 4B
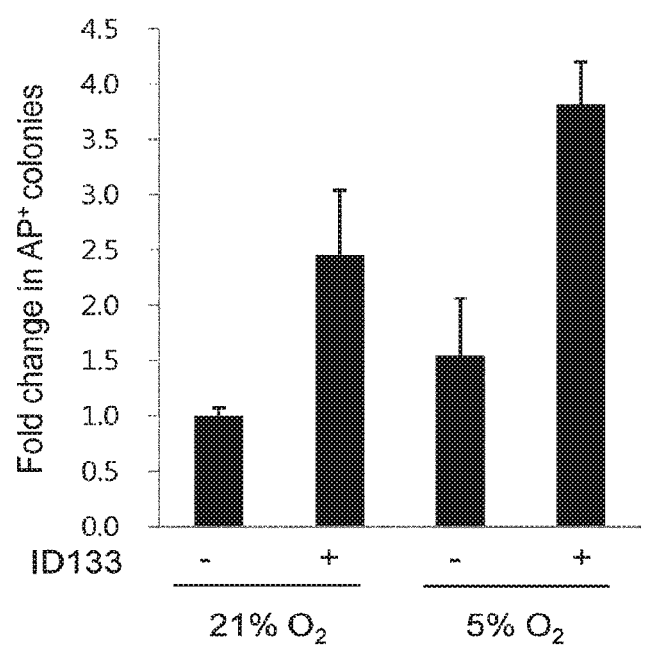
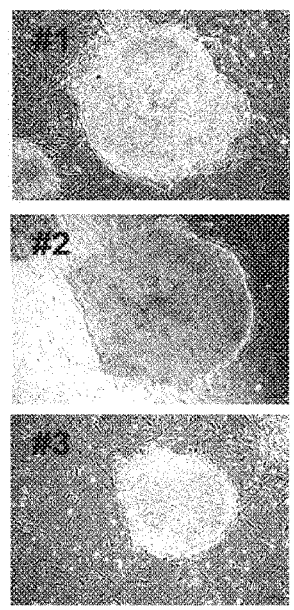

HPLC data

Method: 75%- 0% $H_2O$, 35 min

Eluent A: Acetonitrile, B: $H_2O$ (0.05% TFA)

|   | Name | Retention Time | Area | % Area | Height |
|---|------|----------------|------|--------|--------|
| 1 | RSC-133 | 7.752 | 3953976 | 100 | 593095 |

Method: 80%- 0% $H_2O$, 35 min

Eluent A: Acetonitrile, B: $H_2O$ (0.05% TFA)

|   | Name | Retention Time | Area | % Area | Height |
|---|------|----------------|------|--------|--------|
| 1 | RSC-133 | 10.152 | 8408893 | 100 | 1512967 |

LOW-MOLECULAR-COMPOUND FOR IMPROVING PRODUCTION, MAINTENANCE AND PROLIFERATION OF PLURIPOTENT STEM CELLS, COMPOSITION COMPRISING THE SAME, AND CULTURE METHOD

RELATED APPLICATIONS

This application is a division of U.S. patent application Ser. No. 14/358,672, filed May 15, 2014, which is a 35 U.S.C. § 371 filing of International Patent Application No. PCT/KR2012/009420, filed Nov. 8, 2012, which claims priority to Korean Patent Application No. 10-2012-0056881, filed May 29, 2012, and Korean Patent Application No. 10-2012-0057803, filed May 30, 2012, the entire disclosures of which are hereby incorporated herein by reference.

TECHNICAL FIELD

The present invention relates to an indoleacrylic acid-based novel compound of formula 1, a cell culture medium comprising the same, a composition for promoting reprogramming comprising the same, a cell culture comprising the same, and a method for producing and maintaining reprogrammed pluripotent stem cells using the same.

BACKGROUND ART

As used herein, the term "stem cell" generally refers to cells that have excellent self-renewal potential while maintaining an undifferentiated state and are capable of differentiating in a tissue-specific manner so as to have certain functions and shapes under certain environments and conditions. Human pluripotent stem cells, including human embryonic stem cells and human induced pluripotent stem cells, are capable of self-renewal under suitable in vitro culture conditions and have a pluripotent ability to differentiate into all types of cells of the body. Due to such characteristics, the results of studies on these pluripotent stem cells have been applied not only for the understanding of biological basic knowledge, including the development, differentiation and growth of organisms, but also for the development of cell therapy agents for fundamental treatment of various diseases and the development of new drugs. While efforts have been increasingly made to develop practically applicable technology based on human pluripotent stem cells in various fields, there are still problems to be solved in terms of efficiency, safety and economy in a process for the production and proliferative culture of human pluripotent stem cells. Specifically, it is required to develop a technology for producing large amounts of undifferentiated and differentiated stem cells, which can satisfy the demand for the stem cells at any time. Particularly, for the development of cell therapy agents, it is necessary to ensure cell culture technology, which has excellent performance, can provide clinically applicable cells and is highly efficient.

Generally, undifferentiated human pluripotent stem cells can be continuously cultured by co-culturing with feeder cells such as mouse embryonic fibroblasts (MEFs) or in feeder-free conditions using conditioned media (CM) obtained from cultures of MEFs or chemically defined media. However, co-culture with animal feeder cells or the use of conditioned media from animal feeder cells involves the risk of transmitting one or more infectious agents such as viruses to human pluripotent stem cells. For this reason, in recent years, continued efforts have been made to develop chemically defined media containing known components such as low-molecular-weight compounds, peptides or the like without containing animal feeder cells or sera and apply these chemically defined media for the production and culture of human pluripotent stem cells. These chemically defined media have significantly contributed to the growth of the stem cell market.

Embryonic stem cells derived from the inner cell mass of frozen-thawed embryos are extracted from frozen-thawed embryos to be discarded, and thus pose no legal problems. However, because these cells are extracted from embryos, these cells pose ethical and religious issues from the viewpoint of life's destruction. In addition, because these cells are derived from limited embryos, transplant rejection cannot be avoided due to the lack of immune compatibility between individuals. As an alternative to overcome such problems, a method of producing induced pluripotent stem cells having characteristics almost similar to those of embryonic stem cells from adult stem cells using reprogramming factors was recently successfully developed (Cell 126, 663-676, 2006; Cell 131, 861-872, 2007; Nature 441, 1061-1067, 2006; Nature 451, 141-146, 2008). Due to the development of this method, the expectation of development of practically applicable stem cell technology based on pluripotent stem cells is increasing. Particularly, induced pluripotent stem cells do not require embryos for the production thereof, the use of the patient's own extracted stem cells does not pose the problem of immune rejection, and thus induced pluripotent stem cells are technically highly useful. However, in order to allow the current technology to enter the stage of practical stage, it is necessarily required to develop technology capable of replacing the use of virus in order to overcome the problems of the current technology, including low efficiency of reprogramming and low clinical safety.

As methods for improving the efficiency of reprogramming, examples of success in increasing the efficiency of reprogramming by the control of extracellular environments or the use of additives such as low-molecular-weight compounds have been reported. In addition, it was reported that the efficiency of reprogramming of somatic cells is effectively increased in a hypoxic condition similar to the environment of embryonic stem cells (Cell Stem Cell, 5: 237-241, 2009). Also, Dr. Ding's team (Shi et al., Cell Stem Cell, 2008) reported that low-molecular-weight compounds such as BIX-01294 (G9a histone methyltransferase inhibitor) and BayK8644 (L-type calcium channel agonist), RG108(DNA methyltransferase inhibitor) are effective in increasing the efficiency of reprogramming, and Dr. Melton's team (Huangfu et al., Nat Biotechnol, 2008) reported that low-molecular-weight compounds such as VPA (histone deacetylase inhibitor), TSA (histone deacetylase inhibitor) and SAHA (histone deacetylase inhibitor are effective in increasing the efficiency of reprogramming. With respect to the development of alternatives to the use of virus, the following study results were reported: 1) transient expression technology utilizing a single nonviral polycistronic vector (Gonzalez et al, PNAS USA, 2009; Chang et al, Stem cells, 2009); 2) adenoviral transfection technology (Stadtfeld et al, Science 2008); 3) establishment of iPSC using a single nonviral polycistronic vector through the development of a Cre/loxP recombinant expression control system (Soldner et al, Cell, 2009), and removal of a reprogramming cassette by Cre transfection (Kaji et al, Nature, 2009), 4) a piggyback (PB) transposon system (Woltjen et al, Nature, 2009; Kaji et al, Nature, 2009), and 5) nonintegrating episomal vectors (Yu et al, Science, 2009). However, the possibility of genetic abnormalities and tumorigenesis still exists.

Accordingly, the present inventors have conducted extensive studies to discover not only low-molecular-weight compounds capable of improving the technology for the maintenance and culture of undifferentiated human pluripotent stem cells, but also low-molecular-weight compounds capable of improving the reprogramming technology of producing human pluripotent stem cells from somatic cells. As a result, the present inventors have discovered the novel low-molecular-weight compound RSC-133 and have verified that the use of a medium composition containing RSC-133 significantly increases the efficiency of reprogramming for producing human pluripotent stem cells and significantly improves culture conditions for maintaining and proliferating human pluripotent stem cells in an undifferentiated state, thereby completing the present invention.

DISCLOSURE

Technical Problem

It is an object of the present invention to provide a novel compound of formula 1 or a pharmaceutically acceptable salt thereof.

Another object of the present invention is to provide a cell culture medium comprising the novel compound of formula 1 or a pharmaceutically acceptable salt thereof.

Still another object of the present invention is to provide a composition for promoting the reprogramming of differentiated cells into pluripotent stem cells, the composition comprising the novel compound of formula 1 or a pharmaceutically acceptable salt thereof.

Still another object of the present invention is to provide an in vitro cell culture comprising: differentiated cells; the composition for promoting reprogramming; and a reprogramming factor, wherein the differentiated cells are reprogrammed into pluripotent stem cells.

Still another object of the present invention is to provide a method of producing reprogrammed pluripotent cells from differentiated cells, the method comprising the steps of: (a) transferring a reprogramming factor to the differentiated cells; and (b) culturing the differentiated cells in a medium containing the composition for promoting reprogramming.

Still another object of the present invention is to provide a cell culture medium capable of improving the maintenance and proliferation of undifferentiated pluripotent stem cells.

Still another object of the present invention is to provide a method of culturing pluripotent stem cells in an undifferentiated state.

Still another object of the present invention is to provide a cell culture medium capable of improving the maintenance and proliferation of undifferentiated pluripotent stem cells.

Still another object of the present invention is to provide an in vitro cell culture comprising: pluripotent stem cells; and the cell culture medium serving to maintain the pluripotent stem cells in an undifferentiated state by a plurality of continuous subcultures.

Technical Solution

In order to accomplish the above objects, in one aspect, the present invention provides a compound of the following formula 1 or a pharmaceutically acceptable salt thereof:

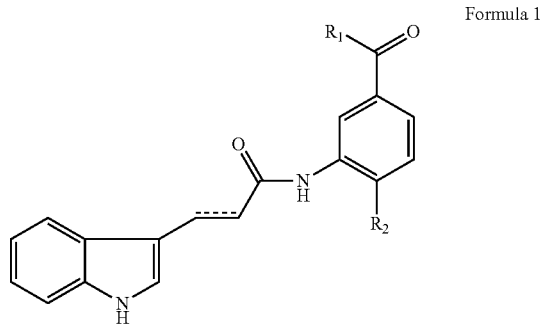

Formula 1 wherein $R_1$ is a methoxy group ($OCH_3$), an amino group ($NH_2$), a methylamino group ($NHCH_3$), a dimethylamino group ($N(CH_3)_2$), an O-isopropyl group, a propylamino group ($NHCH(CH_3)_2$), a hydroxyl group (OH), $NHCH_2$-furan, $NHCH_2CH_2$-piperidine, or $NH(CH_2)_3$-morpholine; $R_2$ is a hydroxyl group (OH) or hydrogen (H); and the portion indicated by - - - may be a single or double bond.

In an embodiment, in formula 1, $R_1$ may be a methoxy group ($OCH_3$); $R_2$ may be hydrogen; and the portion indicated by - - - may be a double bond.

In another embodiment, in formula 1, $R_1$ may be an amino group ($NH_2$); $R_2$ may be hydrogen; and the portion indicated by - - - may be a double bond.

In still another embodiment, in formula 1, $R_1$ may be a methylamino group ($NHCH_3$); $R_2$ may be hydrogen; and the portion indicated by - - - may be a double bond.

In still another embodiment, in formula 1, $R_1$ may be a dimethylamino group ($N(CH_3)_2$); $R_2$ may be hydrogen; and the portion indicated by - - - may be a double bond.

In still another embodiment, in formula 1, $R_1$ may be an amino group ($NH_2$); $R_2$ may be hydrogen; and the portion indicated by - - - may be a single bond.

In still another embodiment, in formula 1, $R_1$ may be O-isopropyl; $R_2$ may be a hydroxyl group (OH); and the portion indicated by - - - may be a double bond.

In still another embodiment, in formula 1, $R_1$ may be an amino group ($NH_2$); $R_2$ may be a hydroxyl group (OH); and the portion indicated by - - - may be a double bond.

In still another embodiment, in formula 1, $R_1$ may be a methylamino group ($NHCH_3$); $R_2$ may be a hydroxyl group (OH); and the portion indicated by - - - may be a double bond.

In still another embodiment, in formula 1, $R_1$ may be a propylamino group ($NHCH(CH_3)_2$); $R_2$ may be a hydroxyl group (OH); and the portion by - - - may be a double bond.

In still another embodiment, in formula 1, $R_1$ may be a dimethylamino group ($NH(CH_3)_2$); $R_2$ may be a hydroxyl group (OH); and the portion indicated by - - - may be a double bond.

In still another embodiment, in formula 1, $R_1$ may be a hydroxyl group (OH); $R_2$ may be hydrogen; and the portion indicated by - - - may be a double bond.

In still another embodiment, in formula 1, $R_1$ may be $NHCH_2$-furan; $R_2$ may be hydrogen; and the portion indicated by - - - may be a double bond.

In still another embodiment, in formula 1, $R_1$ may be $NHCH_2CH_2$-piperidine; $R_2$ may be hydrogen; and the portion indicated by - - - may be a double bond.

In still another embodiment, in formula 1, $R_1$ may be $NH(CH_2)_3$-morpholine; $R_2$ may be hydrogen; and the portion indicated by - - - may be a double bond.

In still another embodiment, in formula 1, R₁ may be O-isopropyl; R₂ may be hydrogen; and the portion indicated by - - - may be a double bond.

In an embodiment, preferred examples of the compound of formula 1 according to the present invention include the following compounds 1) to 15):
1) methyl 3-[3-(1H-indol-3-yl)acrylamido]benzoate;
2) 3-[3-(1H-indol-3-yl)acrylamido]benzamide;
3) 3-[3-(1H-indol-3-yl)acrylamido]-N-methylbenzamide;
4) 3-[3-(1H-indol-3-yl)acrylamido]-N,N-dimethylbenzamide;
5) 3-(3-1H-indol-3-yl-propionylamino)-benzamide;
6) isopropyl 3-[3-(1H-indol-3-yl)acrylamido]-4-hydroxybenzoate;
7) 3-[3-(1H-indol-3-yl)acrylamido]-4-hydroxybenzamide);
8) 3-[3-(1H-indol-3-yl)acrylamido]-4-hydroxy-N-methylbenzamide;
9) 3-[3-(1H-indol-3-yl)acrylamido]-4-hydroxy-N-isopropylbenzamide;
10) 3-[3-(1H-indol-3-yl)acrylamido]-4-hydroxy-N,N-dimethylbenzamide;
11) 3-[3-(1H-indol-3-yl)acrylamido]benzoic acid;
12) 3-[3-(1H-indol-3-yl)acrylamido]-N-(furan-2-ylmethyl)benzamide;
13) 3-(3-1H-Indol-3-yl-acryloylamino)-N-(2-piperidin-1-yl-ethyl)-benzamide;
14) 3-(3-1H-Indol-3-yl-acryloylamino)-N-(3-morpholin-4-yl-propyl)-benzamide; and
15) isopropyl 3-[3-(1H-indol-3-yl)acrylamido]benzoate.

The compounds of formula 1 according to the present invention may be prepared in the form of pharmaceutically acceptable salts or solvates using conventional methods known in the art.

The salt is preferably an acid addition salt formed by a pharmaceutically acceptable free acid. The acid addition salt is prepared according to a conventional method. For example, it is prepared by dissolving the compound in an aqueous solution of an excess of acid and precipitating the formed salt using a water-miscible organic solvent, for example, methanol, ethanol, acetone or acetonitrile. Alternatively, it may be prepared by heating the same molar amounts of the compound and acid or alcohol (e.g., glycol monomethylether) in water, and then drying the mixture by evaporation or filtering the precipitated salt by suction.

Herein, the free acid may be organic acid or inorganic acid. Examples of the inorganic acid include, but are not limited to, hydrochloric acid, phosphoric acid, sulfuric acid, nitric acid and tartaric acid. Examples of the organic acid include, but are not limited to, methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid and hydroiodic acid.

In addition, the compounds of formula 1 according to the present invention may be prepared in the form of pharmaceutically acceptable metal salts using bases. An alkali metal or alkaline earth metal salt may be prepared, for example, by dissolving the compound in a solution of an excess of alkali metal hydroxide or alkaline earth metal hydroxide, filtering out undissolved compound salt, and then drying the filtrate by evaporation. For pharmaceutical purposes, the metal salt prepared is preferably sodium, potassium or calcium salt, but is not limited thereto. In addition, a silver salt corresponding to the metal salt can be obtained by reacting an alkali metal or alkaline earth metal salt with a suitable silver salt (e.g., silver nitrate).

Pharmaceutically acceptable salts of the compound of formula 1 include, unless otherwise indicated, a salt of an acidic or basic group, which can be present in the compound of formula 1. Examples of pharmaceutically acceptable salts include sodium, calcium and potassium salts of a hydroxyl group, and other pharmaceutically acceptable salts of an amino group include hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts. These salts can be prepared by methods known in the art.

Preferably, the compound of the present invention may be 3-[3-(1H-indol-3-yl)-acrylamido]-benzamide having a structure of the following formula 2:

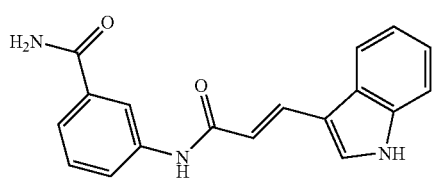

Formula 2

The compound of formula 2 that is an indole derivative may be named "3-(3-1H-Indol-3-yl)-acrylamido)-benzamide)" (hereinafter also referred to as Reprogramming Stimulating Compound-133, RSC-133, ID-133). It is a novel compound discovered during analog library screening of trans-3-indoleacrylic acid-based compounds. In a process of reprogramming mouse fibroblasts, the cells were treated with each of 39 trans-3-indoleacrylic acid-based compounds, and two compounds having an excellent effect of improving reprogramming efficiency were selected. Also, 32 new trans-3-indoleacrylic acid-based compounds having similar chemical structures, including the two selected compounds, were selected and analyzed for the effect of improving the efficiency of reprogramming of human fibroblasts, and based on the results of the analysis, reprogramming stimulating compound (RSC)-133 having an excellent effect of improving the efficiency of reprogramming was selected.

In an example of the present invention, in order to prepare the RSC-133 compound, trans-3-indoleacrylic acid and 3-amino-benzamide were dissolved in DMF, and then benzotriazol-1-yl-N-oxy-tris(pyrrolidino)-phosphonium hexafluorophosphate (PyBOP) and N,N-diisopropylethylamine (DIPEA) were added to the solution. The reaction solution was stirred overnight at room temperature. The stirred solution was separated and purified to obtain 3-[3-(1H-indol-3-yl)-acrylamido]-benzamide (RSC-133) as a yellow solid (Example 1-2).

In another aspect, the present invention provides a cell culture medium comprising the compound of formula 1 or a pharmaceutically acceptable salt thereof. Preferably, the compound of formula 1 may be 3-[3-(1H-indol-3-yl)-acrylamido]-benzamide (RSC-133) or a pharmaceutically acceptable salt thereof.

As used herein, the term "cell culture medium" refers to a medium capable of supporting the growth and survival of stem cells under in vitro culture conditions and is meant to include all conventional media, which are suitable for the culture of cells and used in the art. Thus, the term "cell culture medium" means a material that is added to a culture medium, such as the compound of formula 1 or a pharmaceutically acceptable salt thereof, in order to culture cells or achieve specific purposes. The composition of the culture medium and culture conditions may be selected depending on the kind of cells. The culture medium that is used for cell culture is preferably a cell culture minimum medium (CCMM) that generally contains a carbon source, a nitrogen source and trace elements. Examples of the cell culture minimum medium include, but are not limited to, DMEM (Dulbecco's Modified Eagle's Medium), MEM (Minimal essential Medium), BME (Basal Medium Eagle), RPMI1640, F-10, F-12, α-MEM (α-Minimal essential Medium), GMEM (Glasgow's Minimal essential Medium), and Iscove's Modified Dulbecco's Medium, etc.

In still another aspect, the present invention provides a composition for promoting the reprogramming of differentiated cells into pluripotent stem cells, the composition comprising the compound of formula 1 or a pharmaceutically acceptable salt thereof. Preferably, the compound of formula 1 may be 3-[3-(1H-indol-3-yl)-acrylamido]-benzamide (RSC-133) or a pharmaceutically acceptable salt thereof.

As used herein, the term "differentiation" refers to a phenomenon in which the structure or function of cells is specialized during the division, proliferation and growth thereof. That is, the term refers to a process in which the feature or function of cell or tissue of an organism changes in order to perform work given to the cell or tissue. For example, a process in which pluripotent stem cells such as embryonic stem cells change to ectoderm, mesoderm and endoderm cells is also defined as differentiation, and in a narrow sense, a process in which hematopoietic stem cells change to red blood cells, white blood cells, platelets or the like also corresponds to differentiation.

As used herein, the term "differentiated cells" refers to cells that undergone the differentiation process so as to have a specific shape and function. Differentiated cells that are used in the present invention are not specifically limited, but are preferably somatic cells or progenitor cells. In addition, differentiated cells are human cells.

As used herein, the term "somatic cells" refers to any differentiated cells other than germ cells, which constitute animals or plants and have a chromosome number of 2n.

As used herein, the term "progenitor cells" refers to undifferentiated progenitor cells which do not express a differentiated differentiation phenotype when their progeny cells express a specific differentiated phenotype. For example, progenitor cells for neurons are interneurons, and progenitor cells for myotube cells are myoblast.

As used herein, the term "pluripotent stem cells" refers to cells that are capable of differentiating into all the tissues of the body and have self-renewal potential and include embryonic stem cells and induced pluripotent stem cells, but is not limited thereto. Pluripotent stem cells in the present invention include those derived from humans, monkeys, pigs, horses, cattle, sheep, dogs, cats, mice, rabbits or the like. Preferably, pluripotent stem cells are human pluripotent stem cells.

As used herein, the term "embryonic stem cells" refers to pluripotent or totipotent cells that are obtained by in vitro culture of inner cell masses extracted from blastocysts immediately before implantation into the uterus of the mother, are capable of differentiating into all the tissues of the body, and have self-renewal potential. In a broad sense, the term also includes embryoid bodies derived from embryonic stem cells. Embryonic stem cells in the present invention include embryonic stem cells derived from humans, monkeys, pigs, horses, cattle, sheep, dogs, cats, mice, rabbits or the like, and are preferably human embryonic stem cells.

As used herein, the term "induced pluripotent stem cells" (iPSCs) refers to cells induced from differentiated cells by an artificial reprogramming process so as to have pluripotent differentiation potential and is also referred to as reprogrammed stem cells. The artificial reprogramming process may be performed by the use of a virus-mediated vector such as retrovirus or lentivirus or a nonviral vector or by introduction of nonvirus-mediated reprogramming factors using proteins and cell extractsor the like, or includes a reprogramming process that is performed by stem cell extracts, compounds or the like. Induced pluripotent stem cells have properties almost similar to those of embryonic stem cells. Specifically, induced pluripotent stem cells show similarity in cell morphology and expression patterns of gene and protein to those of embryonic stem cells, have pluripotency in vitro and in vivo, form teratomas, and generate chimeric mice upon injection into mouse blastocysts, and are capable of germline transmission of gene. Induced pluripotent stem cells in the present invention include those derived from any animals, including humans, monkeys, pigs, horses, cows, sheep, dogs, cats, mice, rabbits, etc., and are preferably human induced pluripotent stem cells.

As used herein, the term "reprogramming" or "dedifferentiation" refers to a process in which differentiated cells can be restored into cells having a new type of differentiation potential. In the present invention, the term "reprogramming" is used in the same meaning as cell reprogramming. This cell reprogramming mechanism involves the removal of epigenetic (DNA state associated with changes in gene function that occur without a change in the nucleotide sequence) marks in the nucleus, followed by establishment of a different set of marks, and different cells and tissues acquire different gene expression programs during the differentiation and growth of multicellular organisms.

As used herein, the term "promoting the reprogramming" means increasing the rate of reprogramming or the efficiency of reprogramming in the reprogramming process. That is, the term includes increasing the efficiency of reprogramming in terms of speed and rate.

The inventive composition for promoting the reprogramming of differentiated cells into pluripotent stem cells comprises RSC-133 at a concentration that does not impair the survival and function of cells. Preferably, the composition comprises 0.01-50 µM of RSC-133. More preferably, it comprises 0.1-20 µM of RSC-133. Most preferably, it comprises 8-12 µM of RSC-133.

The inventive composition for promoting the reprogramming of differentiated cells into pluripotent stem cells may further comprise reprogramming factors. As used herein, the term "reprogramming factor" refers to a material that induces the reprogramming of differentiated cells into induced pluripotent stem cells having a new type of differentiation potential. The reprogramming factor may be any material that induces the reprogramming of differentiated stem cells, and it may be selected depending on the kind of cells to differentiate. Preferably, the reprogramming factor that is used in the composition of the present invention may be one or more proteins selected from the group consisting of Oct4, Sox2, KlF4, c-Myc, Nanog and Lin-28 or one or more nucleic acid molecules encoding these proteins. More preferably, the reprogramming factor may be Oct4 protein or a nucleotide molecule encoding the protein. Particularly, the composition may comprise Oct4, Sox2 and KlF4 proteins or nucleic acid molecules encoding these proteins.

The composition of the present invention is preferably in the form of culture medium. Thus, materials that are generally contained in cell culture media may additionally be added to the composition of the present invention, as long as they do not interfere with the reprogramming of differentiated cells into pluripotent stem cells.

In an example of the present invention, the effects of the above-described 39 trans-3-indoleacrylic acid-based compounds on the promotion of induction of reprogramming were analyzed in mouse skin fibroblasts, and as a result, it was shown that the addition of the novel compound RSC-133 or ID-558 effectively increased the efficiency of reprogramming compared to a control (FIGS. 1A and 1B). When the effects of the compounds were analyzed comparatively with known reprogramming-promoting compounds (Valproic acid, 5-azacytidine, BIX-01294, etc.), it was shown that the novel compound RSC-133 most effectively increased the efficiency of reprogramming (FIGS. 2A and 2B).

In an example of the present invention, the effects of thirty-two novel trasn-3-indoleacrylic acid-based compounds, including the novel compound RSC-133 and ID-558 confirmed to effectively induce the reprogramming of mouse skin fibroblasts, on the induction of reprogramming, were analyzed, and as a result, it was shown that the efficiency of reprogramming of human skin fibroblasts treated with the novel compound RSC-133 was effectively increased compared to that of a control group (FIG. 3).

In an example of the present invention, it was shown that the use of the novel compound RSC-133 not only in normal culture conditions (21% $O_2$), but also in hypoxic culture conditions (5% $O_2$), increased the efficiency of reprogramming compared to that of a control (FIGS. 4A and 4B). Several research groups reported that hypoxic culture conditions (5% $O_2$) are more effective in the maintenance of pluripotency and the induction of reprogramming than normal culture conditions (21% $O_2$), and it was found that the addition of RSC-133 can additionally improve the culture conditions of pluripotent stem cells and the conditions of reprogramming of differentiated cells to pluripotent stem cells (FIGS. 4A and 4B).

In another example of the present invention, examination was carried out to determine whether the novel low-molecular-weight compound RSC-133 can substitute for an existing reprogramming factor (c-Myc) when the reprogramming of human skin fibroblasts into reprogrammed stem cells is induced by addition of the compound RSC-133. It is known that c-Myc is an oncogenic gene and that the re-expression of c-Myc viral gene in the reprogrammed stem cells formed after induction of reprogramming is involved in carcinogenesis. Thus, studies on reprogramming methods excluding c-Myc have received attention. In the present invention, it was found that, although RSC-133 alone does not show the effect of substituting for c-Myc, the use of RSC-133 in combination with sodium butyrate (NaB) can substitute for c-Myc and can also increase the efficiency of reprogramming compared to that of a control (FIG. 5).

In conclusion, the novel low-molecular-weight compound RSC-133 was confirmed to be a factor that effectively increases the efficiency of reprogramming of mouse and human somatic cells.

In still another example of the present invention, the efficiencies of induction of reprogramming at different concentrations of RSC-133 were examined to determine the optimal RSC-133 concentration range effective for increasing the efficiency of reprogramming, and as a result, it was shown that the efficiency of reprogramming was increased in a manner dependent on the concentration of RSC-133 (FIG. 8). Specifically, according to the culture conditions shown in the upper portion of FIG. 8, human skin fibroblasts were transduced with OSKM virus, and then, as shown in the graph in the lower portion of FIG. 8, changes in the efficiency of reprogramming at different concentrations (0 µM, 0.1 µM, 1 µM, 5 µM, 10 µM and 20 µM) of RSC-133 were examined. The efficiency of reprogramming at each concentration of RSC-133 was determined by measuring the number of colonies that were positive in pluripotency-specific alkaline phosphatase (AP) staining and had a hESC-like morphology. The experimental results indicated that RSC-133 could increase the efficiency of reprogramming in a concentration-dependent manner at a concentration of up to 10 µM (FIG. 8). It was shown that, when the concentration of RSC-133 was increased to 20 µM, the efficiency of reprogramming was not additionally increased (FIG. 8). In addition, it was verified that, when human skin fibroblasts were treated with RSC-133 at a concentration up to 50 µM, RSC-133 did not induce cytotoxicity (FIG. 9).

In still another example of the present invention, in order to optimize the timing and period of RSC-133 treatment in a reprogramming protocol, RSC-133 was added under various conditions, and then changes in the efficiency of reprogramming were examined (FIG. 10).

As a result, it was shown that, when treatment with RSC-133 was performed for 5 days in each of four divided steps consisting of step 1 (5 days after viral infection; condition 4 in FIG. 10), step 2 (5-10 days after viral infection; condition 7 in FIG. 10), step 3 (10-15 days after viral infection; condition 8 in FIG. 10) and step 4 (15-20 days after viral infection; condition 9 in FIG. 10 9), treatment with RSC-133 together with a reprogrammed-cell culture medium in step 1 (for 5 days immediately after viral infection) most effectively increased the efficiency of reprogramming (FIG. 10). In addition, it was shown that, when treatment with RSC-133 was performed for 10 days in each of three divided steps consisting of step 1 (10 days after viral infection; condition 3 in FIG. 10), step 2 (5-15 days after viral infection; condition 6 in FIG. 10) and step 3 (10-20 days after viral infection; condition 10 in FIG. 10), treatment with RSC-133 in step 1 (for 10 days immediately after viral infection; culture in reprogrammed-cell culture medium for 5 days, followed by culture in human embryonic stem cell culture medium in a fresh culture dish for days; condition 3 in FIG. 10) most effectively increased the efficiency of reprogramming (FIG. 10). Additionally, it was shown that, when treatment with RSC-133 was performed for 15 days in each of two divided steps consisting of step 1 (15 days after viral infection; condition 2 in FIG. 10) and step 2 (5-20 days after viral infection; condition 5 in FIG. 10), the efficiency of reprogramming was increased in all the two conditions (FIG. 10). Among all the conditions tested, continuous treatment with RSC-133 throughout the process of inducing reprogramming showed the highest increase in the efficiency of reprogramming (condition 1 in FIG. 10). In conclusion, it was verified that, when treatment with RSC-133 is performed in the initial stage of the reprogramming process, it showed the best effect on the induction of reprogramming, and even treatment with RSC-133 is performed after the initial stage of the reprogramming process, it can significantly increase the efficiency of reprogramming in a manner dependent on the time of treatment.

In still another example of the present invention, whether the novel compound RSC-133 has the effect of promoting the growth and proliferation of cells in a culture process for inducing reprogramming was examined by measuring the total number of cells at various time points (FIG. 11). It could be seen that an increase in the number of cells transduced with OSKM was significantly slow compared to that of a control group not treated with OSKM and that treatment with the novel compound RSC-133 under the same conditions promoted the growth of the cells (FIG. 12). In addition, a change in the proliferation of cells during a culture process for inducing reprogramming was examined by a BrdU assay. As a result, it was shown that treatment with the novel compound RSC-133 significantly improved the cell growth in a manner dependent on the time of treatment, similar to the above-described results (FIGS. 13 to 15).

In still another example of the present invention, in order to examine whether the novel compound RSC-133 can promote kinetics in a culture process for reprogramming to shorten the time required for the induction of reprogramming, the expression patterns of pluripotency-specific markers were analyzed at various time points. As can be seen in FIGS. 15 and 16, the results of immunostaining analysis (FIG. 15) and real-time PCR analysis (FIG. 16) indicated that, when reprogramming was induced after treatment with the novel compound RSC-133, the expression of pluripotency-specific markers (Nanog, Tra1-81, Oct4, and Rex1) appeared early than that in an untreated control group, suggesting that the novel compound RSC-133 can stimulate reprogramming kinetics to effectively shorten the time required for the induction of reprogramming.

In still another example of the present invention, in order to examine whether the novel compound RSC-133 can alleviate the senescence that is induced by OSKM transduction known as an obstacle in the process for inducing reprogramming, changes in the expression patterns of p53, p21 and p16 that are signaling factors known to play an important role in the induction of aging were measured (FIG. 16) and a SA-β-Gal assay was performed (FIG. 17). As can be seen in FIG. 16, the aging senescence factors p53, p21 and p16 were effectively inhibited in culture medium containing the novel compound RSC-133, and as can be seen in FIG. 17, treatment with RSC-133 resulted in a significant decrease in SA-β-Gal-positive cells. These results suggest that the inhibition of senescence factors by RSC-133 contributes to improvement in conditions of the induction of reprogramming.

In still another example of the present invention, in order to examine whether the novel compound RSC-133 is associated with an epigenetic change required for the reprogramming process, H3K9 acetylation that is epigenetic activation associated with the pluripotent state of stem cells was analyzed. As can be seen in FIG. 18, the results of Western blot analysis by immunostaining indicated that H3K9 acetylation was increased in culture medium containing the novel compound RSC-133, suggesting that RSC-133 induces epigenetic activation in the reprogramming process. In addition, the results of measurement of enzymatic activity and Western blot analysis indicated that the increase in H3K9 acetylation is associated with the inhibition of HDAC (particularly HDAC1) activity (FIG. 19) and HDAC1 expression (FIG. 21), which is induced by RSC-133. In addition, it was shown that the activity of DNA methyl transferase 1 (DNMT1) contributing to DNA methylation was significantly inhibited by RSC-133 (FIG. 20).

In still another example of the present invention, it was found that pluripotent stem cells produced using medium containing the novel compound RSC-133 maintained their hESC-like morphology during the continuous culture process and expressed pluripotency-specific markers at levels similar to those in hESC (FIGS. 22 and 23) and showed the methylation of pluripotency-specific promoters (Oct4 and Nanog) (FIG. 24). In addition, it was verified that four transgenes (OSKMs) used in the induction of reprogramming were all integrated into the genome of the host cells (FIG. 25) and that the pluripotent stem cells maintained a normal karyotype (FIG. 26) and has the ability to differentiate into three germ layers in vitro and in vivo (FIG. 27).

In another aspect, the present invention provides an in vitro cell culture comprising: differentiated cells; the above-described composition for promoting reprogramming; and a reprogramming factor, wherein the differentiated cells are reprogrammed into pluripotent stem cells.

More specifically, the present invention encompasses all in vitro cell cultures obtained by treating differentiated cells with the reprogramming-promoting composition comprising the compound of formula 1 and with a reprogramming factor. The in vitro cell culture also comprises various cells which are in the reprogramming process, various proteins, enzymes and transcripts which are obtained during culture of the cells, and culture media containing them. Preferably, the compound of formula 1 may be 3-[3-(1H-indol-3-yl)-acrylamido]-benzamide (RSC-133) or a pharmaceutically acceptable salt thereof.

The differentiated cells and pluripotent stem cells of the present invention are as described above.

The reprogrammed cells can show characteristics in that the function of HDAC1 is inhibited and the level of H3K9ace is increased, compared to a control group not treated with the composition.

In still another aspect, the present invention provides a method for producing reprogrammed stem cells from differentiated cells, the method comprising the steps of: (a) transferring a reprogramming factor to the differentiated cells; and (b) culturing the differentiated cells in a medium containing the above-described composition for promoting reprogramming.

Step (a) of transferring the reprogramming factor to the differentiated cells may be performed by any method that is generally used in the art to provide nucleic acid molecules or proteins to cells. Preferably, step (a) may be performed by a method of adding the reprogramming factor to a culture of the differentiated cells, a method of injecting the reprogramming factor directly into the differentiated cells, or a method of infecting the differentiated cells with a virus obtained from packaging cells transfected with a viral vector including a gene of the reprogramming factor.

The method of injecting the reprogramming factor directly into the differentiated cells may be performed using any method known in the art. This method can be suitably selected from among microinjection, electroporation, particle bombardment, direct injection into muscles, an insulator-based method, and a transposon-based method, but is not limited thereto.

The reprogramming factor that is used in the present invention is as described above.

In the present invention, the packaging cells may be selected from among various cells known in the art depending on the kind of viral vector used. Preferably, the packaging cells may be GP2-293 packaging cells, but are not limited thereto.

In addition, the viral vector that is used in the present invention may be selected from among vectors derived from retroviruses, for example, HIV (human immunodeficiency virus), MLV (murine leukemia virus), ASLV (avian sarcoma/leukosis), SNV (spleen necrosis virus), RSV (rous sarcoma virus), MMTV (mouse mammary tumor virus) or the like, lentiviruses, adenovirus, adeno-associated virus, herpes simplex virus, etc, but is not limited thereto. Preferably, the viral vector may be a retroviruse vector. More preferably, it may be the retroviruse vector pMXs.

Steps (a) and (b) may be performed simultaneously, sequentially or in the reverse order. The above-described method may further comprise a step of isolating embryonic stem cell-like colonies from the culture resulting from step (b).

In still another aspect, the present invention provides a composition for maintaining and culturing pluripotent stem cells in an undifferentiated state, the composition comprising the compound of formula 1 or a pharmaceutically acceptable salt thereof. In the present invention, pluripotent stem cells can be maintained in an undifferentiated state by the use of the composition comprising the compound of formula 1 or a pharmaceutically acceptable salt thereof.

In an example of the present invention, H9 human embryonic stem cells that are typical human pluripotent stem cells were cultured in unconditioned medium (UM) in which the differentiation of the cells would be easily induced, and the cells were treated with the novel compound RSC-133 in order to examine whether the treatment of the cells with the compound can inhibit the induction of differentiation of the cells and maintain the cells in an undifferentiated state. As can be seen in FIG. 28, in the culture medium treated with the novel compound RSC-133, the induction of differentiation was inhibited, and the differentiated state was improved to the level of cells cultured in conditioned medium (CM). In addition, it was verified that, in the culture medium treated with RSC-133, the expression levels of pluripotency-specific markers was maintained at the levels of the factors in cells cultured in CM, and particularly, H3K9 acetylation associated with epigenetic activation was maintained at a level similar to that of undifferentiated hESC cultured in CM (FIG. 29), suggesting that RSC-133 is effective in maintaining and improving the undifferentiated state of human pluripotent stem cells.

In the present invention, the composition of formula 1 or a pharmaceutically acceptable salt thereof may be used in an amount sufficient for maintaining pluripotent stem cells in an undifferentiated state. The cell culture medium for culturing undifferentiated pluripotent stem cells preferably comprises RSC-133 in a concentration of 0.01-50 µM. More preferably, it comprises RSC-133 at a concentration of 0.1-20 µM. Most preferably, it comprises RSC-133 at a concentration of 5-15 µM.

In addition, the cell culture medium according to the present invention may further comprise one or more selected from the group consisting of an N2 supplement, a B27 supplement, bFGF and TGF. Herein, the N2 supplement and the B27 supplement may be provided at a ratio of 1:1, and the bFGF may be provided at a concentration of 4-100 ng/ml. Also, the TGF may be provided at a concentration of 1-10 ng/ml.

Moreover, the cell culture medium according to the present invention may further comprise one or more components of a chemically defined medium known in the art. The addition of RSC-133 can improve the composition and effect of the chemically defined medium.

In still another aspect, the present invention provides a method for establishing an embryonic stem cell line capable of being maintained in an undifferentiated state, the method comprising the steps of: obtaining embryonic stem cells; and culturing the embryonic stem cells under culture conditions including the cell culture medium to obtain the embryonic stem cell line.

Herein, the embryonic stem cells include embryonic stem cells derived from any animals, including humans, monkeys, pigs, horses, cattle, sheep, dogs, cats, mice, rabbits and the like. Preferably, the embryonic stem cells are human embryonic stem cells.

In still another aspect, the present invention provides a method of culturing pluripotent stem cells in an undifferentiated state, the method comprising culturing the pluripotent stem cells in a medium comprising the above-described cell culture medium for maintaining and culturing pluripotent stem cells in an undifferentiated state.

The use of the above-described method can maintain embryonic stem cells in an undifferentiated state in the presence or absence of animal serum and feeder cells.

Herein, the embryonic stem cells include embryonic stem cells derived from any animals, including humans, monkeys, pigs, horses, cattle, sheep, dogs, cats, mice, rabbits and the like. Preferably, the embryonic stem cells are human embryonic stem cells.

In still another aspect, the present invention provides an in vitro cell culture comprising: pluripotent stem cells; and the above-described cell culture medium serving to maintain the pluripotent stem cells in an undifferentiated state by a plurality of continuous subcultures.

The scope of the in vitro cell culture according to the present invention encompasses all in vitro cell cultures obtained by treating pluripotent stem cells with the RSC-133-containing composition for maintaining and culturing pluripotent stem cells in an undifferentiated state. The in vitro cell culture also comprises various cells which are in a culture process, various proteins, enzymes and transcripts which are obtained during culture of the cells, and culture media containing them.

Pluripotent stem cells that are used in the present invention are as described above.

Advantageous Effects

According to the present invention, when the novel low-molecular-weight compound RSC-133 is added in a culture process for producing reprogrammed pluripotent stem cells from human differentiated cells, it can increase the efficiency of reprogramming and can significantly reduce the time required for the induction of reprogramming. Particularly, the novel compound RSC-133 can substitute for c-Myc acting as both a reprogramming factor and an oncogenic factor, and it can effectively increase the efficiency of reprogramming in both normal oxygen culture conditions and hypoxic culture conditions. In addition, RSC-133 can inhibit the induction of aging occurring in the reprogramming process, exhibits the effect of promoting cell proliferation, and induces epigenetic activation to improve culture conditions for induction of reprogramming. The present invention will contribute to optimizing a process of producing induced pluripotent stem cells from a small amount of patient-specific somatic cells obtained from various sources, and thus it will significantly improve a process of developing clinically applicable personalized stem cell therapy agents and new drugs and will facilitate the practical use of these agents and drugs. In addition, the novel low-molecular-weight compound RSC-133 can provide a cell culture medium effective for maintaining the undifferentiated state of human embryonic stem cells that are typical pluripotent stem cells. The cell culture medium containing RSC-133 can effectively induce the proliferation of human pluripotent stem cells in an undifferentiated state and can be effectively

DESCRIPTION OF DRAWINGS

FIG. 1A shows an experimental process of inducing the reprogramming of mouse embryonic fibroblasts. Oct4 (O), Sox2 (S), Klf4 (K), and cMyc (M). FIG. 1B is a graph showing the increase in efficiency of reprogramming by RSC-133 and ID-558 among screened compounds. The values shown on the graph are mean values. The data are expressed as mean±SD (n=3).

FIGS. 4A and 4B show that the novel low-molecular-weight compound 133 increased the efficiency of reprogramming of human skin fibroblasts compared to that of a control group not only in normal conditions (21% $O_2$), but also in hypoxic conditions (5% $O_2$). According to previous reports, the efficiency of reprogramming increases in hypoxic conditions. The novel compound 133 can exhibit a synergistic effect in the reprogramming process promoted by such hypoxic conditions. FIG. 4A is a graph showing the results of measurement of AP activity. FIG. 4B shows the morphology of reprogrammed stem cells induced by the addition of the novel compound 133 under hypoxic conditions.

MODE FOR INVENTION

Figure 1A:
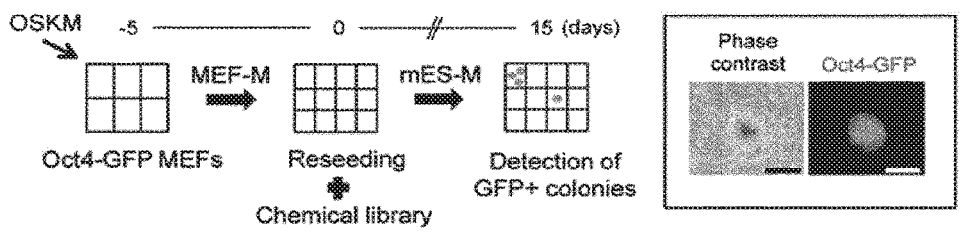
FIGS. 1A and 1B show a process of screening mouse cell reprogramming factors using analog library screening of novel trans-3-indoleacrylic acid-based compounds. In order to screen low-molecular-weight compounds that promote the production of reprogrammed stem cells, mouse embryonic stem cells (OG2-MEF; hemizygous for the Oct4-GFP transgene) were transduced with reprogramming viruses (Oct4, Sox2, Klf4, and c-Myc). After 5 days, the cells were seeded on gelatin-coated plates and then cultured in mouse embryonic stem cell culture media containing each of low-molecular-weight compounds until colonies having a morphology similar to that of mouse embryonic stem cells were formed. After 15 days, the number of colonies expressing endogenous Oct4 GFP fluorescence was measured, and compounds that increased the efficiency of reprogramming compared to that of a control group were selected.

Hereinafter, the present invention will be described in further detail with reference to examples. It is to be understood, however, that these examples are for illustrative purposes only and are not intended to limit the scope of the present invention.

Example 1: Group of Low-Molecular-Weight Compounds 1-1. Method for Synthesis of Low-Molecular-Weight Compounds Low-molecular-weight compounds, including RSC-133 (3-(3-1H-indol-3-yl-acryloylamino)-benzamide), were synthesized by the method shown in the following reaction scheme 1:

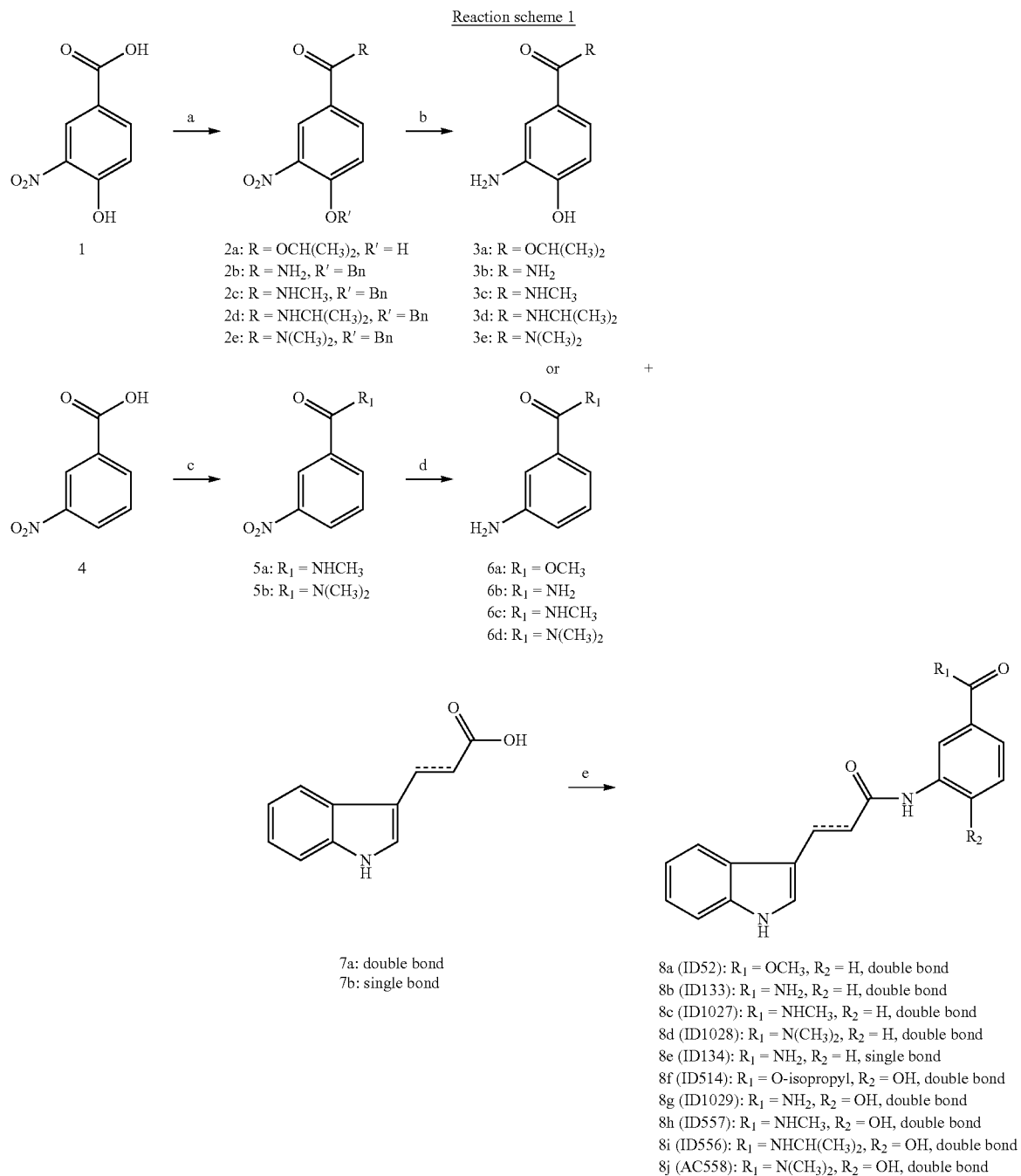

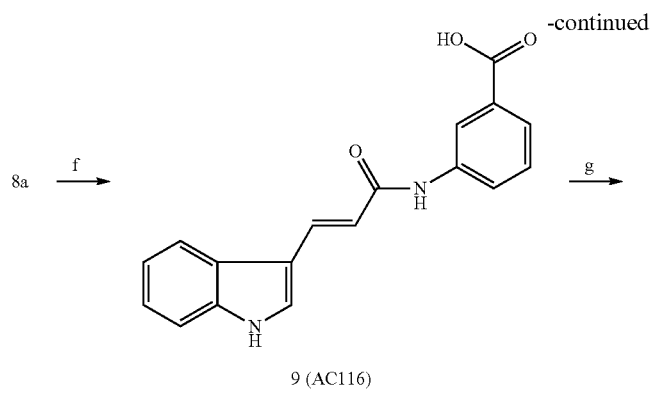

9 (AC116)

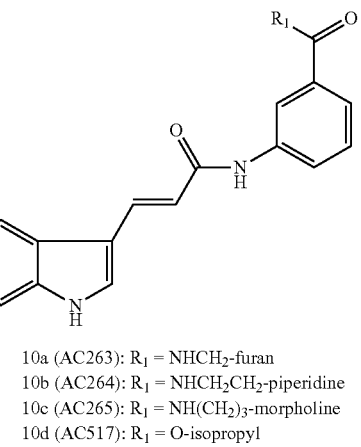

10a (AC263): R$_1$ = NHCH$_2$-furan
10b (AC264): R$_1$ = NHCH$_2$CH$_2$-piperidine
10c (AC265): R$_1$ = NH(CH$_2$)$_3$-morpholine
10d (AC517): R$_1$ = O-isopropyl The reactants and reaction conditions in reaction scheme 1 are as follows: a) 2a is H$_2$SO$_4$; 2b to 2e are i) SOCl$_2$, MeOH; ii) BnBr, K$_2$CO$_3$, DMF; iii) LiOH, THF, H$_2$O; iv) NH$_4$Cl, EDC, HOBt, DIPEA, DMF (2b); NH$_2$CH$_3$, NH$_2$CH(CH$_3$)$_2$, or NH(CH$_3$)$_2$, 50% PPAA, Et$_3$N, acetonitrile (2c-e); b) H$_2$, 5% Pd/C, MeOH; c) 5a to 5b are NH$_2$CH$_3$, or NH(CH$_3$)$_2$, 50% PPAA, Et$_3$N, acetonitrile; d) H$_2$, 10% Pd/C, MeOH; e) EDC, HOAt, or HOBt, DIPEA, DMF; PyBOP, DIPEA, DMF; DCC, DIPEA, THF; f) LiOH, THF/H$_2$O; g) 10a to 10c are furfuryamine, 2-piperidin-1-yl-ethylamine, or 3-morpholin-4-yl-propylamine, HATU, DIPEA, DMF; 10d is 2-bromopropane, ionic liquid, DMF.

In this synthesis process, all commercial compounds were grade-1 reagents and were used without additional purification. Solutions were dried according to standard procedures. All reactions were performed in a flame-dried glass apparatus in an atmosphere of dry argon at a pressure of 1 atm. Quantum nuclear magnetic resonance (1H-NMR) spectra were measured in Varian (400 MHz or 300 MHz) spectrometer. Unless otherwise specified, materials resulting from all reactions were purified either by flash column chromatography using silica gel 60 (230-400 mesh Kieselgel 60) or by thin layer chromatography using glass-backed silica gel plates (1 mm thickness). In addition, reactions were monitored by thin layer chromatography on 0.25 mm silica plates (E. Merck, silica gel 60 F254). Chromatograms were visualized by exposure to iodine vapor and immersion in PMA or Hanessian solution, followed by exposure to UV light. Isopropyl 4-hydroxy-3-nitrobenzoate corresponding to compound 2a in the above reaction scheme was prepared in the following manner. First, sulfuric acid (98% H$_2$SO$_4$) was added dropwise to a solution of 4-hydroxy-3-nitrobenzoic acid (2.0 g, 10.9 mmol) in 2-propylalcohol (25 mL) at 0° C., and the solution was refluxed in the presence of argon for 48 hours. After completion of the reaction, the reaction mixture was concentrated under reduced pressure. The resulting material was purified by silica gel column chromatography (n-hexane: EtOAc=5:1) to afford 2.11 g of isopropyl 4-hydroxy-3-nitrobenzoate (2a) as a yellow solid. $^1$H NMR (CDCl$_3$, 300 MHz) δ=10.87 (s, 1H), 8.79 (d, J=1.2 Hz, 1H), 8.23 (dd, J=1.8 Hz, 8.7 Hz, 1H), 7.22 (t, J=11.7 Hz, 1H), 5.30 (s, 2H), 5.26 (m, 1H), 1.38 (d, J=6.6 Hz, 6H).

4-Benzyloxy-3-nitrobenzamide corresponding to compound 2b in the above reaction scheme was prepared in the following manner. First, to a solution of 4-benzyloxy-3-nitrobenzoic acid 1-3 (1 g, 3.6 mmol) and ammonium chloride (294 mg, 5.5 mmol) in DMF (15 mL), EDC (842 mg, 4.4 mmol), HOBt (593 mg, 4.4 mmol) and DIPEA (1.6 mL, 9.15 mmol) were added. The reaction solution was stirred overnight at room temperature and cooled with water, followed by extraction with EA. The resulting material was purified by silica gel column chromatography (n-hexane: EA=7:3) to afford the desired compound (980 mg). $^1$H NMR (CDCl$_3$, 400 MHz) δ=8.39 (d, J=2.4 Hz, 1H), 8.08 (dd, J=2.0 Hz, 8.4 Hz, 1H), 7.32-7.46 (m, 5H), 7.16 (d, J=8.8 Hz, 1H), 5.30 (s, 2H).

Amide compounds 2c to 2e in the above reaction scheme were prepared in the following manner. 4-benzyloxy-3-nitrobenzoic acid (500 mg, 1.0 equiv) was suspended in acetonitrile and Et$_3$N (4.0 equiv), and 50% PPAA (1.2 equiv) was added thereto. The mixture was stirred at room temperature for 30 minutes, and each of suitable amines was added thereto. Then, the reaction solutions were stirred overnight, and then dried by evaporation. The resulting materials were purified by column chromatography to afford compounds 2c-2e.

1) 4-Benzyloxy-N-methyl-3-nitrobenzamide (2c) was obtained as a white solid. $^1$H NMR (CDCl$_3$, 300 MHz) δ=8.24 (d, J=2.1 Hz, 1H), 7.99 (dd, J=2.4 Hz, 9.0 Hz, 1H), 7.34-7.46 (m, 5H), 7.17 (d, J=8.7 Hz, 1H), 6.14 (br s, 1H), 5.30 (s, 2H), 3.02 (d, J=5.1 Hz, 3H).

2) 4-Benzyloxy-N-isopropyl-3-nitrobenzamide (2d) was obtained as a white solid. $^1$H NMR (CDCl$_3$, 300 MHz) δ=8.21 (d, J=2.1 Hz, 1H), 7.99 (dd, J=2.1 Hz, 8.7 Hz, 1H), 7.32-7.46 (m, 5H), 7.16 (d, J=8.7 Hz, 1H), 5.89 (d, J=7.2 Hz, 1H), 5.30 (s, 2H), 4.27 (m, 1H), 1.27 (d, J=6.6 Hz, 6H).

3) 4-Benzyloxy-N,N-dimethyl-3-nitrobenzamide (2e) was obtained as a white solid. $^1$H NMR (CDCl$_3$, 300 MHz) δ=7.96 (d, J=1.5 Hz, 1H), 7.63 (dd, J=2.1 Hz, 8.7 Hz, 1H), 7.34-7.46 (m, 5H), 7.15 (d, J=8.7 Hz, 1H), 5.28 (s, 2H), 3.07 (br s, 6H).

Compounds 2a to 2e were reduced in the following manner to prepare compounds 3a to 3e. Each of compounds 2a to 2e was dissolved in anhydrous MeOH, and then 5% palladium carbon was added thereto under an argon atmosphere. Each of the reaction solutions was stirred overnight in a hydrogen atmosphere and filtered through a celite pad, and the filtrates were concentrated without additional purification to obtain crude products.

1) Isopropyl 3-amino-4-hydroxybenzoate (3a) was obtained as a light yellow solid from compound 2a. $^1$H NMR (CDCl$_3$, 300 MHz) δ=7.43 (s, 1H), 7.38 (d, J=8.7 Hz, 1H), 6.74 (d, J=8.1 Hz, 1H), 5.19 (m, 1H), 1.33 (d, J=6.6 Hz, 6H).

2) 3-Amino-4-hydroxybenzamide (3b) was obtained as a brown semi-solid from compound 2b. $^1$H NMR (DMSO-d6, 400 MHz) δ=7.48 (s, 1H), 7.11 (d, J=8.7 Hz, 1H), 6.95 (dd, J=2.0 Hz, 8.4 Hz, 1H), 6.84 (br s, 1H), 6.61 (d, J=8.4 Hz, 1H).

3) 3-Amino-4-hydroxy-N-methylbenzamide (3c) was obtained as a light yellow solid from compound 2c. $^1$H NMR (DMSO-d6, 300 MHz) δ=7.96 (d, J=4.5 Hz, 1H), 7.10 (d, J=2.1 Hz, 1H), 6.92 (dd, J=2.1 Hz, 8.1 Hz, 1H), 6.63 (d, J=8.1 Hz, 1H), 4.61 (br s, 2H), 2.70 (d, J=4.5 Hz, 3H).

4) 3-Amino-4-hydroxy-N-isopropylbenzamide (3d) was obtained as a light yellow solid from compound 2d. $^1$H NMR (DMSO-d6, 300 MHz) δ=7.73 (d, J=8.1 Hz, 1H), 7.10 (d, J=1.5 Hz, 1H), 6.94 (dd, J=2.1 Hz, 8.1 Hz, 1H), 6.62 (d, J=7.8 Hz, 1H), 4.60 (br s, 2H), 4.03 (m, 1H), 1.11 (d, J=6.6 Hz, 6H).

5) 3-Amino-4-hydroxy-N,N-dimethylbenzamide (3e) was obtained as a light yellow solid from compound 2e. $^1$H NMR (DMSO-d6, 300 MHz) δ=9.36 (b, 1H), 6.65 (d, J=1.5 Hz, 1H), 6.63 (d, J=8.4 Hz, 1H), 6.46 (dd, J=2.1 Hz, 7.8 Hz, 1H), 4.64 (br s, 2H), 2.92 (s, 6H).

Amide compounds 5a to 5b in the above reaction scheme were prepared in the following manner. 3-Nitrobenzoic acid (400 mg, 1.0 equiv) was suspended in acetonitrile and Et$_3$N (4.0 equiv), and 50% PPAA (1.2 equiv) was added thereto. The mixture was stirred at room temperature for 30 minutes, and each of suitable amines was added thereto. Then, the reaction solutions were stirred overnight, and then dried by evaporation. The resulting materials were purified by column chromatography to afford compounds 5a-5b. 1)N-methyl-3-nitrobenzamide (5a) was obtained as a white solid. $^1$H NMR (CDCl$_3$, 400 MHz) δ=8.58 (s, 1H), 8.35-8.37 (m, 1H), 8.16 (d, J=8.0 Hz, 1H), 5.19 (t, J=7.6 Hz 1H), 6.23 (br s, 1H), 3.07 (d, J=4.8 Hz).

2) N,N-dimethyl-3-nitrobenzamide (5b) was obtained as a white solid. $^1$H NMR (CDCl$_3$, 400 MHz) δ=8.29 (s, 1H), 8.27 (d, J=2.4 Hz, 1H), 7.77 (d, J=7.6 Hz, 1H), 7.62 (t, J=7.6 Hz 1H), 3.15 (s, 3H), 3.01 (s, 3H).

Meanwhile, methyl 3-aminobenzoate (6a) and 3-aminobenzamide (6b) are commercially available.

Compound 5a or 5b was reduced in the following manner to prepare compound 6c or 6d. Nitrogen-substituted compound 5a or 5b was dissolved in anhydrous MeOH, and 5% palladium carbon was added thereto under an argon atmosphere. The reaction solution was stirred overnight in a hydrogen atmosphere and filtered through a celite pad, and the filtrate was purified without additional purification to obtain a crude product.

1) 3-Amino-N-methylbenzamide (6c) was obtained as a white solid from compound 5a. $^1$H NMR (DMSO-d6, 400 MHz) δ=8.13 (d, J=4.0 Hz, 1H), 6.99-7.05 (m, 2H), 6.89 (d, J=7.2 Hz, 1H), 6.62-6.65 (m, 1H), 5.17 (s, 2H), 2.71 (d, J=4.8 Hz, 3H).

2) 3-Amino-N,N-dimethylbenzamide (6d) was obtained as a white solid from compound 5b. $^1$H NMR (DMSO-d6, 400 MHz) δ=7.02 (t, J=7.6 Hz, 1H), 6.55-6.58 (m, 1H), 6.51 (s, 1H), 6.43 (d, J=7.6 Hz, 1H), 5.18 (s, 2H), 2.89 (d, J=11.6 Hz, 6H).

The above-prepared compounds 3a to 3e or compounds 6a to 6d were reacted with trans-3-indoleacrylic acid (7a) or 3-(1H-indole-3-yl)-propionic acid (7b) to obtain compounds 8a to 8j, compound 9 and compounds 10a to 10d as shown in the above reaction scheme. Methods for preparing these compounds will be described in detail below.

1-2. Method for Synthesis of Low-Molecular-Weight Compound RSC-133 (8b)

Among the above-described low-molecular-weight compounds, RSC-133 (3-[3-(1H-indol-3-yl)-acrylamido]-benzamide (8b)) was synthesized in the following manner.

Figure 6:
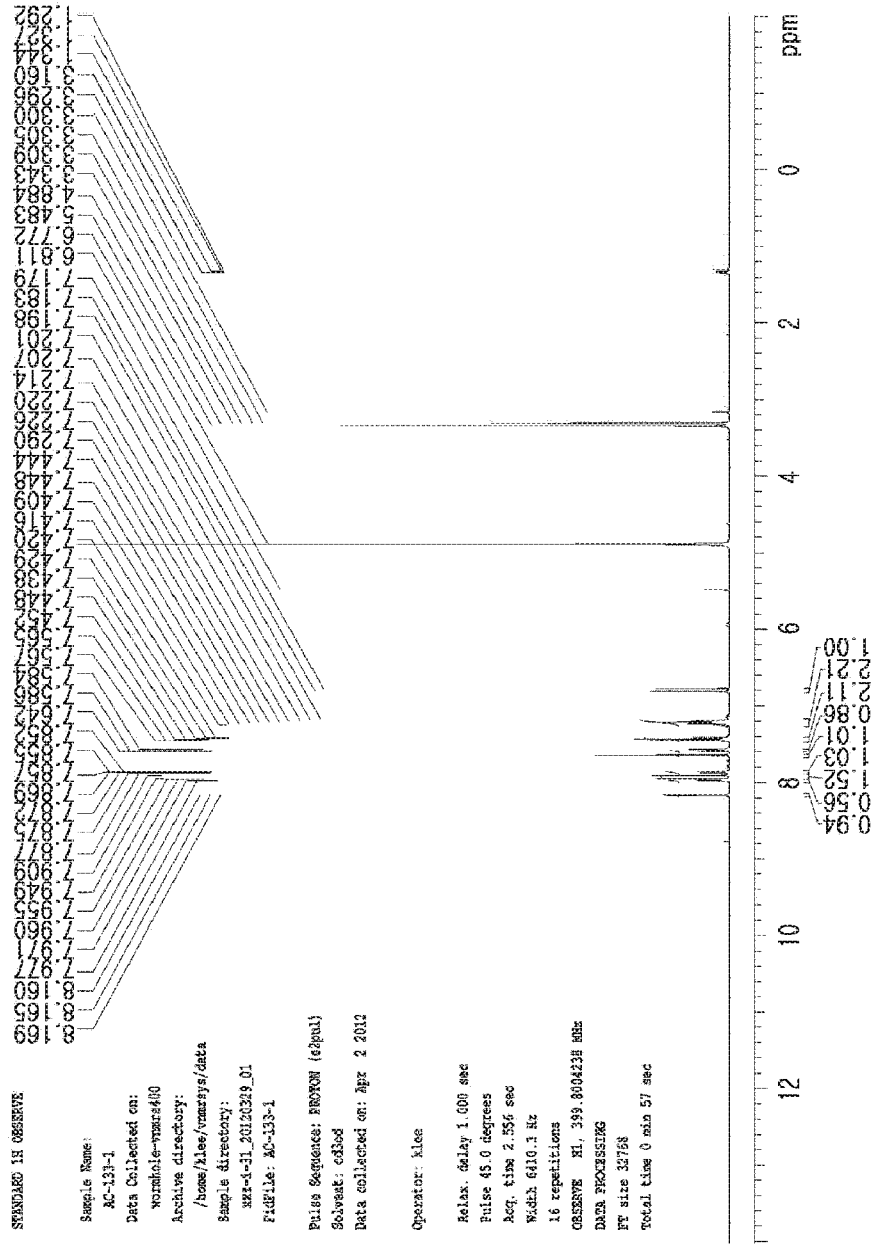
FIG. 6 shows the $^1$H NMR data of RSC-133.
Figure 7:
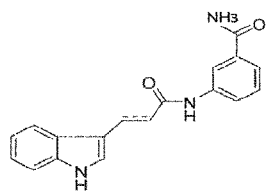
FIG. 7 shows HPLC data relating to the purity of RSC-133.
Figure 7:
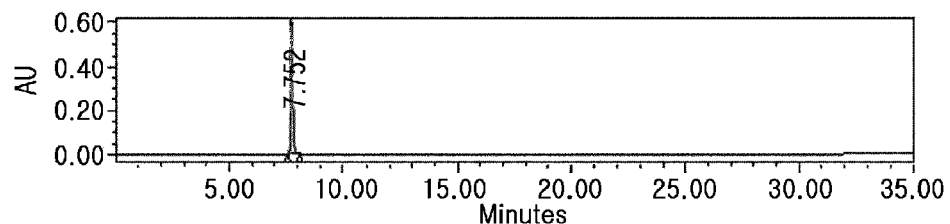
Figure 7:
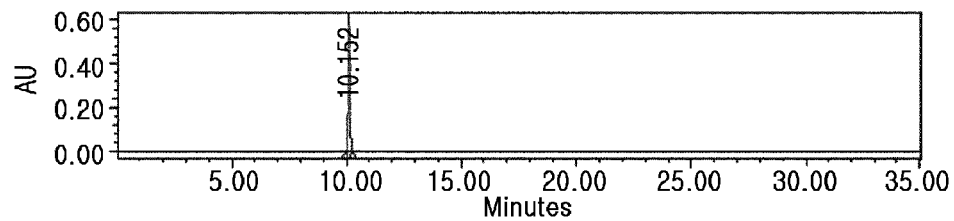

First, trans-3-indoleacrylic acid (7a) and 3-amino-benzamide (6b) were dissolved in DMF, and benzotriazol-1-yl-N-oxy-tris(pyrrolidino)-phosphonium hexafluorophosphate (PyBOP) and N,N-diisopropylethylamine (DIPEA) were added to the solution to perform a coupling reaction. The reaction solution was stirred overnight at room temperature. The resulting material was separated and purified to obtain 3-[3-(1H-indol-3-yl)-acrylamido]-benzamido (RSC-133) as a yellow solid. The chemical characteristics and purity of RSC-133 were analyzed by $^1$H NMR (FIG. 6) and HPLC (FIG. 7). $^1$H NMR (CDCl$_3$, 300 MHz) d=8.90 (s, 1H), 8.21 (s, 1H), 7.86-8.03 (m, 4H), 7.76 (d, J=8.1 Hz, 1H), 7.36-7.41 (m, 3H), 7.20 (m, 2H), 6.60 (d, J=15.3 Hz, 2H), 3.88 (s, 3H).

RSC-133 (3-[3-(1H-indol-3-yl)-acrylamido]-benzamide) synthesized in this Example has a structure of the following formula 2:

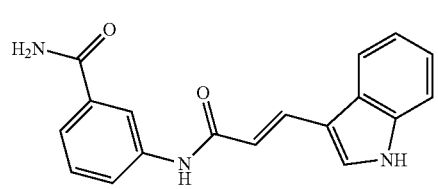

Formula 2

1-3. Synthesis of Low-Molecular-Weight Compound ID-52 (8a)

Among the above-described low-molecular-weight compounds, ID-52 (3-(3-1H-indol-3-yl-acryloylamino)-benzoic acid methyl ester (8a)) was prepared in the following manner. Trans-3-indoleacrylic acid (7a, 150 mg, 0.8 mmol) and 3-amino-benzoic acid methyl ester (6a, 218 mg, 1.44 mmol) were dissolved in DMF, and 1-[3-(dimethyamino) propyl]-3-ethylcarbodiimide hydrochloride (EDC, 230 mg, 1.2 mmol), hydroxy-7-azabenotriazole (HOAT, 163 mg, 1.2 mmol) and N,N-diisopropylethylamine (DIPEA, 0.21 mL, 1.2 mmol) were added to the solution to cause a coupling reaction. The reaction solution was stirred overnight at room temperature. Then, the resulting material was separated and purified to obtain 3-(3-1H-indol-3-yl-acryloylamino)-benzoic acid methyl ester (ID-52) as a yellow solid. $^1$H NMR (CDCl$_3$, 300 MHz) d=8.90 (s, 1H), 8.21 (s, 1H), 7.86-8.03 (m, 4H), 7.76 (d, J=8.1 Hz, 1H), 7.36-7.41 (m, 3H), 7.20 (m, 2H), 6.60 (d, J=15.3 Hz, 2H), 3.88 (s, 3H).

1-4. Synthesis of Low-Molecular-Weight Compound ID-1027 (8c)

Among the above-described low-molecular-weight compounds, ID-1027 (3-[3-(1H-indol-3-yl)-acrylamido]-N-methylbenzamide (8c)) was prepared in the following manner. Trans-3-indoleacrylic acid (7a, 300 mg, 1.6 mmol) and 3-amino-N-methylbenzamide (6c, 240 mg, 1.6 mmol) were dissolved in DMF, and PyBOP (1.7 g, 3.2 mmol) and DIPEA (0.84 mL, 4.8 mmol) were added thereto. The reaction solution was stirred overnight at room temperature and fractionated with EA and brine. The organic phase fraction was dried with MgSO$_4$ and concentrated. The resulting material was purified to obtain 3-[3-(1H-indol-3-yl)-acrylamido]-N-methylbenzamide as a yellow solid. $^1$H NMR (CD$_3$OD, 400 MHz) d=8.08 (s, 1H), 7.98 (d, J=15.2 Hz, 1H), 7.91 (d, J=8.0 Hz, 1H), 7.88 (dd, J=1.6 Hz, J=8.4 Hz, 1H), 7.69 (s, 1H), 7.45-7.47 (m, 2H), 7.21-7.27 (m, 2H), 6.78 (d, J=15.6 Hz, 1H).

1-5. Synthesis of Low-Molecular-Weight Compound ID-1028 (8d)

Among the above-described low-molecular-weight compounds, ID-1028 (3-[3-(1H-indol-3-yl)-acrylamido]-N,N-dimethylbenzamide (8d) was prepared in the following manner. Trans-3-indoleacrylic acid (7a, 300 mg, 1.6 mmol) and 3-amino-N,N-dimethylbenzamide (6d, 262.7 mg, 1.6 mmol) were dissolved in DMF, and PyBOP (1.7 g, 3.2 mmol) and DIPEA (0.84 mL, 4.8 mmol) were added thereto. The reaction solution was stirred overnight at room temperature and fractionated with EA and brine. The organic phase fraction was dried with MgSO$_4$ and concentrated. The residue was purified to afford 3-[3-(1H-indol-3-yl)-acrylamido]-N,N-dimethylbenzamide as a yellow solid. $^1$H NMR (CD$_3$OD, 400 MHz) d=7.96 (d, J=8.0 Hz, 1H), 7.92 (d, J=16.0 Hz, 1H), 7.84 (s, 1H), 7.73 (d, J=7.6 Hz, 1H), 7.64 (s, 1H), 7.40-7.45 (m, 2H), 7.18-7.25 (m, 2H), 7.13 (d, J=7.6 Hz, 1H), 6.78 (d, J=15.6 Hz, 1H), 3.11 (s, 3H), 3.04 (s, 3H).

1-6. Synthesis of Low-Molecular-Weight Compound ID-134 (8e)

Among the above-described low-molecular-weight compounds, ID-134 (3-[3-1H-indol-3-yl-propionylamino]benzamide, 8e) was prepared in the following manner. 3-(1H-indol-3-yl)-propionic acid (7b, 189 mg, 1.0 mmol) and 3-amino-benzamide (6b, 68.1 mg, 0.5 mmol) were dissolved in DMF, and PyBOP and DIPEA were added to the solution to perform a coupling reaction. The reaction solution was stirred overnight at room temperature. Then, the resulting material was separated and purified to obtain 3-[3-1H-indol-3-yl-propionylamino]benzamide (ID-134) as a white solid. $^1$H NMR (DMSO-d$_6$, 300 MHz) d=8.02 (s, 1H), 7.75 (d, J=7.8 Hz, 1H), 7.50 (m, 2H), 7.32 (m, 2H), 6.93-7.09 (m, 3H), 3.04 (t, J=7.8 Hz, 2H), 2.68 (t, J=7.2 Hz, 2H).

1-7. Synthesis of Low-Molecular-Weight Compound ID-514 (8f)

The low-molecular-weight compound ID-514 (isopropyl 3-[3-(1H-indol-3-yl)-acrylamido]-4-hydroxybenzoate (8f)) was prepared in the following manner. Trans-3-indoleacrylic acid (7a, 188 mg, 1.01 mmol) and isopropyl 3-amino-4-hydroxybenzoate (3a, 295 mg, 1.51 mmol) were dissolved in DMF, and EDC (290 mg, 1.51 mmol) and 1-hydroxybenzotriazole hydrate (HOBt, 204 mg, 1.51 mmol) were added thereto. The reaction solution was stirred overnight at room temperature. The resulting material was separated and purified to obtain isopropyl 3-[3-(1H-indol-3-yl)-acrylamido]-4-hydroxybenzoate (ID-514) as a yellow solid. $^1$H NMR (DMSO-d$_6$, 300 MHz) d=11.65 (s, 1H), 11.07 (s, 1H), 9.60 (s, 1H), 8.65 (d, J=1.5 Hz, 1H), 8.11 (d, J=6.6 Hz, 1H), 7.83 (d, J=2.1 Hz, 1H), 7.79 (d, J=15.3 Hz, 1H), 7.57 (dd, J=1.5 Hz, 8.1 Hz, 1H), 7.47 (d, J=7.5 Hz, 1H), 7.19-7.25 (m, 2H), 7.12 (d, J=15.3 Hz, 1H), 6.96 (d, J=8.1 Hz, 1H), 5.10 (m, 1H), 1.31 (d, J=6.6 Hz, 6H).

1-8. Synthesis of Low-Molecular-Weight Compound ID-1029 (8g)

The low-molecular-weight compound ID-1029 (3-[3-(1H-indol-3-yl)-acrylamido]-4-hydroxybenzamide (8g)) was prepared in the following manner. Trans-3-indoleacrylic acid (7a, 300 mg, 1.6 mmol) and 3-amino-4-hydroxybenzamide (3b, 243 mg, 1.6 mmol) were dissolved in DMF, and PyBOP (1.7 g, 3.2 mmol) and DIPEA (0.84 mL, 4.8 mmol) were added thereto. The reaction solution was stirred overnight at room temperature. The resulting material was separated and purified to obtain 3-[3-(1H-indol-3-yl)-acrylamido]-4-hydroxybenzamide (ID-1029) as a yellow solid. $^1$H NMR (CD$_3$OD, 400 MHz) d=8.08 (s, 1H), 7.98 (d, J=15.2 Hz, 1H), 7.91 (d, J=8.0 Hz, 1H), 7.88 (dd, J=1.6 Hz, J=8.4 Hz, 1H), 7.69 (s, 1H), 7.45-7.47 (m, 2H), 7.21-7.27 (m, 2H), 6.78 (d, J=15.6 Hz, 1H).

1-9. Synthesis of Low-Molecular-Weight Compound ID-557 (8h)

The low-molecular-weight compound ID-557 (3-[3-(1H-indol-3-yl)-acrylamido]-4-hydroxy-N-methylbenzamide (8h)) was prepared in the following manner. DCC (220 mg, 1.07 mmol) and DIPEA (0.2 mL, 1.07 mmol) were added to a solution of trans-3-indoleacrylic acid (7a, 100 mg, 0.53 mmol) in THF. The reaction solution was stirred at room temperature for 30 minutes while 3-amino-4-hydroxy-N-methylbenzamide (3c, 106 mg, 0.64 mmol) was added thereto. The reaction solution was stirred overnight. The resulting material was separated and purified to obtain 3-[3-(1H-indol-3-yl)-acrylamido]-4-hydroxy-N-methylbenzamide (ID-557) as a yellow solid. $^1$H NMR (acetone-d$_6$, 300 MHz) d=10.88 (b, 1H), 9.61 (b, 1H), 8.03 (d, J=15.6 Hz, 1H), 8.02 (d, J=2.4 Hz, 1H), 7.94 (d, J=2.1 Hz, 2H), 7.87 (d, J=2.4 Hz, 2H), 7.52-7.59 (m, 3H), 7.20-7.28 (m, 2H), 7.08 (d, J=15.3 Hz, 1H), 6.93 (d, J=8.1 Hz, 1H), 3.62 (q, J=6.6 Hz, 1H), 2.88 (d, J=4.5 Hz, 3H).

1-10. Synthesis of Low-Molecular-Weight Compound ID-556 (8i)

The low-molecular-weight compound ID-556 (3-[3-(1H-indol-3-yl)-acrylamido]-4-hydroxy-N-isopropylbenzamide (8i)) was prepared in the following manner. DCC (220 mg, 1.07 mmol) and DIPEA (0.2 mL, 1.07 mmol) were added to a solution of trans-3-indoleacrylic acid (7a, 100 mg, 0.53 mmol) in THF. The mixture was stirred at room temperature for 30 minutes while 3-amino-4-hydroxy-N-isopropylbenzamide (3d, 124 mg, 0.64 mmol) was added thereto. The reaction solution was stirred overnight. The resulting material was separated and purified to obtain 3-[3-(1H-indol-3-yl)-acrylamido]-4-hydroxy-N-isopropylbenzamide (ID-556) as a yellow solid. $^1$H NMR (acetone-d$_6$, 300 MHz) d=10.95 (b, 1H), 10.89 (b, 1H), 9.61 (b, 1H), 8.02 (d, J=15.6 Hz, 1H), 8.01 (s, 1H), 7.88 (t, J=3.0 Hz, 2H), 7.59 (dd, J=2.1 Hz, 8.7 Hz, 1H), 7.54 (dd, J=2.1 Hz, 6.6 Hz, 1H), 7.20-7.28 (m, 3H), 7.08 (d, J=15.3 Hz, 1H), 6.91 (d, J=8.1 Hz, 1H), 4.21 (m, 1H), 1.22 (d, J=6.6 Hz, 6H).

1-11. Synthesis of Low-Molecular-Weight Compound ID-558 (8j)

The low-molecular-weight compound ID-558 (3-[3-(1H-indol-3-yl)-acrylamido]-4-hydroxy-N,N-dimethylbenzamide (8j)) was prepared in the following manner. DCC (220 mg, 1.07 mmol) and DIPEA (0.2 mL, 1.07 mmol) were added to a solution of trans-3-indoleacrylic acid (7a, 100 mg, 0.53 mmol) in THF. The mixture was stirred at room temperature for 30 minutes while 3-amino-4-hydroxy-N,N-dimethylbenzamide (3e, 116 mg, 0.64 mmol) was added thereto. The reaction solution was stirred overnight. The resulting material was separated and purified to obtain 3-[3-(1H-indol-3-yl)-acrylamido]-4-hydroxy-N,N-dimethylbenzamide (ID-558) as a yellow solid. $^1$H NMR (acetone-d$_6$, 300 MHz) d=10.85 (b, 1H), 9.51 (b, 1H), 8.01 (d, J=15.3 Hz, 1H), 7.99-8.02 (m, 1H), 7.86 (d, J=2.1 Hz, 1H), 7.58 (d, J=2.1 Hz, 1H), 7.52-7.55 (m, 1H), 7.21-7.28 (m, 2H), 7.17 (dd, J=1.8 Hz, 8.1 Hz, 1H), 7.03 (d, J=15.6 Hz, 1H), 6.93 (d, J=8.1 Hz, 1H), 3.02 (s, 6H).

1-12. Synthesis of Low-Molecular-Weight Compound ID-116(9)

The low-molecular-weight compound ID-116 (3-[3-(1H-indol-3-yl)-acrylamido]benzoic acid) was prepared in the following manner. 3-[3-(1H-indol-3-yl)-acrylamido]-benzoate (8a, 188 mg, 0.59 mmol) was dissolved in THF/H$_2$O (1:1, 10 mL), and LiOH.H$_2$O (49.3 mg, 1.17 mmol) was added thereto at room temperature. The reaction solution was stirred overnight at room temperature, after which it was acidified with hydrochloric acid and extracted with ethyl acetate (EA). The resulting material was separated and purified to obtain 3-[3-(1H-indol-3-yl)-acrylamido]benzoic acid as a white solid. $^1$H NMR (CD$_3$OD, 300 MHz) d=8.53 (s, 1H), 7.90-7.96 (m, 3H), 7.74 (d, J=7.8 Hz, 1H), 7.58 (s, 1H), 7.41 (m, 2H), 7.19 (m, 2H), 6.78 (d, J=15 Hz, 1H).

1-13. Synthesis of Low-Molecular-Weight Compound ID-263 (10a)

The low-molecular-weight compound ID-263 (3-[3-(1H-indol-3-yl)-acrylamido]-N-(furan-2-yl-methyl)benzamide) was prepared in the following manner. 3-(3-1H-indol-3-yl-acryloylamino)-benzoic acid (9, 500 mg, 1.63 mmol) and furylamine (0.23 mL, 2.45 mmol) were dissolved in DMF, and DIPEA (0.43 mL, 2.45 mmol) and HATU (O-(7-azabenzotriazol-1-yl)-N,N,N'N'-tetramethyluronium hexafluorophosphate (931.6 mg, 2.45 mmol) were added thereto. Then, the reaction solution was stirred overnight at room temperature. The resulting material was separated and purified to obtain 3-[3-(1H-indol-3-yl)-acrylamido]-N-(furan-2-yl-methyl)benzamide (ID-263) as a yellow solid. $^1$H NMR (CD$_3$OD, 300 MHz) d=8.13 (m, 1H), 7.96 (m, 2H), 7.82 (m, 1H), 7.63 (s, 1H), 7.52 (m, 1H), 7.39-7.45 (m, 3H), 7.20 (m, 2H), 6.78 (d, J=15.9 Hz, 1H), 6.32 (m, 2H), 4.56 (s, 2H).

1-14. Synthesis of Low-Molecular-Weight Compound ID-264 (10b)

The low-molecular-weight compound ID-264 (3-(3-1H-indol-3-yl-acrylamino)-N-(2-piperidin-1-yl-ethyl)-benzamide) was prepared in the following manner. 3-(3-1H-indol-3-yl-acryloylamino)-benzoic acid (9, 150 mg, 0.49 mmol) and 2-piperidin-1-yl-erthylamine (0.10 mL, 0.73 mmol) were dissolved in DMF, and HATU (277.6 mg, 0.73 mmol) and DIPEA (0.13 mL, 0.73 mmol) were added thereto. The reaction solution was stirred overnight at room temperature. The resulting material was separated and purified to obtain 3-(3-1H-indol-3-yl-acryloylamino)-N-(2-piperidin-1-yl-ethyl)-benzamide (ID-264) as a yellow solid. $^1$H NMR (DMSO-d$_3$, 300 MHz) d=11.67 (b, 1H), 10.16 (s, 1H), 8.41 (s, 1H), 8.11 (s, 1H), 7.76-7.98 (m, 4H), 7.38-7.50 (m, 3H), 7.23 (m, 2H), 6.84 (d, J=15.9 Hz, 1H) 3.33-3.43 (m, 6H), 2.51 (m, 2H), 1.41-1.54 (m, 6H).

1-15. Synthesis of Low-Molecular-Weight Compound ID-265 (10c)

The low-molecular-weight compound ID-265 (3-(3-1H-indol-3-yl-acrylamino)-N-(3-morpholin-4-yl-propyl)-benzamide) was prepared in the following manner. 3-(3-1H-indol-3-yl-acryloylamino)-benzoic acid (9, 150 mg, 0.49 mmol) and 3-morpholin-4-yl-propylamine (0.11 mL, 0.73 mmol) were dissolved in DMF, and HATU (277.6 mg, 0.73 mmol) and DIPEA (0.13 mL, 0.73 mmol) were added thereto. The reaction solution was stirred overnight at room temperature. The resulting material was separated and purified to obtain 3-(3-1H-indol-3-yl-acryloylamino)-N-(3-morpholin-4-yl-propyl)-benzamide (ID-265) as a yellow solid. $^1$H NMR (DMSO-d$_3$, 300 MHz) d=11.66 (b, 1H), 10.14 (s, 1H), 8.46 (ps-t, J=5.4 Hz, 1H), 8.09 (s, 1H), 7.76-7.98 (m, 4H), 7.37-7.50 (m, 3H), 7.22 (m, 2H), 6.82 (d, J=15.9 Hz, 1H), 3.55-3.59 (m, 4H), 3.27 (m, 1H), 3.16 (d, J=15.9 Hz, 1H), 2.31-2.36 (m, 6H) 1.69 (m, 2H).

1-16. Synthesis of Low-Molecular-Weight Compound ID-517 (10d)

The low-molecular-weight compound ID-517 (isopropyl 3-[3-(1H-indol-3-yl)acrylamido]benzoate) was prepared in the following manner. 3-(3-1H-indol-3-yl-acryloylamino)-benzoic acid (9, 180 mg, 0.59 mmol) and ionic liquid (1.12 g, 1.47 mmol) were dissolved in DMF, and 2-bromopropane (144 mg, 1.18 mmol) and DIPEA (152 mg, 1.18 mmol) were added thereto. The reaction solution was heated at 60° C. for 2 days and cooled with water. The resulting material was separated and purified to obtain isopropyl 3-[3-(1H-indol-3-yl)acrylamido]benzoate (ID-517) as a light yellow solid. $^1$H NMR (DMSO-d$_3$, 300 MHz) d=11.68 (b, 1H), 10.22 (s, 1H), 8.27 (s, 1H), 8.03 (d, J=9.0 Hz, 1H), 7.94-7.98 (m, 1H), 7.85 (s, 1H), 7.80 (d, J=16.2 Hz, 1H), 7.62 (d, J=8.1 Hz, 1H), 7.47 (t, J=7.2 Hz, 2H), 7.19-7.26 (m, 2H), 6.81 (d, J=15.6 Hz, 1H), 5.16 (m, 1H), 1.34 (d, J=6.0 Hz, 6H).

Example 2: Culture of Human Embryonic Stem Cells and Reprogrammed Stem Cells

Human embryonic stem cell (hESC) H9 (NIH Code, WA09; WiCell Research Institute, Madison, Wis.) and reprogrammed stem cells (hiPSC) were generally cultured in hESC culture medium (composed of 80% DMEM/F12, 20% knockout serum replacement (KSR, Invitrogen, Carlsbad, Calif.), 1% non-essential amino acids (NEAA, Invitrogen), 1 mM L-glutamine (Invitrogen), 0.1 mM β-mercaptoethanol (Sigma, St. Louis, Mo.) and 6 ng/ml bFGF (basic fibroblast growth factor, Invitrogen)) on γ-irradiated MEFs (mouse embryonic fibroblasts). The cells were subcultured with 1 mg/ml collagenase IV (Invitrogen) at intervals of 5-6 days. Human newborn foreskin fibroblasts (hFF, ATCC, catalog number CRL-2097; American Type Culture Collection, Manassas, Va.) were cultured in DMEM containing 10% FBS (fetal bovine serum, Invitrogen), 1% non-essential amino acid, 1 mM L-glutamine and 0.1 mM β-mercaptoethanol.

Example 3: Production of Retrovirus and Induction of hiPSC

A pMXs vector comprising the human cDNA of OCT4 (POU5F1), SOX2, c-MYC(MYC) and KlF4, as disclosed in Takahashi, K. et al. (Cell 131, 2007, 861-872), was purchased from Addgene. GP2-293 packaging cells were transfected with retroviral vector DNA and a VSV-G envelop vector using the CalPhos transfection kit. At 24 hours after the transfection, the supernatant containing the first virus was collected, and then the medium was replaced, and after 48 hours, the supernatant containing the second virus was collected.

For production of iPSC, human skin fibroblasts (hFFs) and mouse embryonic fibroblasts (MEFs) were seeded on gelatin-coated 6-well plates at a concentration of 1×10$^5$ cells per well at one day before transfection and were transfected with virus in the presence of polybrene (8 μg/ml). At 5 days after the transfection, hFFs or MEFs were collected by trypsin treatment and seeded again on Matrigel-coated 6-well plates at a concentration of 5 to 6×10$^4$ cells per well in order to perform experiments in feeder-free conditions. The medium was replaced with MEF-CM medium containing 10 ng/ml of bFGF. MEF-CM was prepared as γ-irradiated MEF according to a known method (Xu C. Nat Biotechnol 19, 971-974), and 8 ng/ml bFGF was added to MEF-CM. The medium was replaced at 2-day intervals. At 20 days after the transfection, hESC-like colonies were collected and transferred to 12-well plates having MEFs as feeder cells, and then continuously cultured using the hESC culture method described in Example 2.

Example 4: Screening of Low-Molecular-Weight Compounds

The OSKM reprogramming factor virus was produced according to the method of Example 3. In order to screen low-molecular-weight compounds that increase the efficiency of reprogramming, hFFs and mouse embryonic fibroblasts (OG2-MEF; hemizygous for the Oct4-GFP transgene) were seeded on gelatin-coated 6-well plates at a concentration of $1\times10^5$ cells at one day before transfection, and then transfected with virus in the presence of polybrene (8 μg/ml. At 5 days after the transfection, hFFs or MEFs were collected by trypsin treatment and seeded again on Matrigel- or gelatin-coated 12-well plates at a concentration of $3.5\times10^4$ cells per well in order to perform experiments under feeder-free conditions. The medium was replaced with 10 ng/ml bFGF-containing MEF-CM or mouse embryonic stem cell culture medium, and then the prepared low-molecular-weight compounds that are trans-3-indoleacrylic based compounds were added at various concentrations. The culture medium containing each of the low-molecular-weight compounds was replaced at 2-day intervals. At 15 days after the transfection, the number of either colonies showing AP activity or colonies expressing endogenous Oct4 GFP fluorescence was measured to determine the efficiency of reprogramming.

Example 5: RNA Extraction, Reverse Transcription and PCR Analysis

Total RNA was isolated from the produced cells using RNeasy Mini kit (Qiagen, Valencia, Calif.), and then reverse-transcribed using SuperScript First-strand synthesis system kit (Invitrogen) according to the manufacturer's instruction. Then, semi-quantitative RT-PCR was performed using platinum Taq SuperMix kit (Invitrogen) under the following conditions: initial denaturation at 94° C. for 3 min, and then 25-30 cycles, each consisting of 94° C. for 30 sec, 60° C. for 30 sec and 72° C. for 30 sec, followed by final extension at 72° C. for 10 min.

Example 6: Alkaline Phosphatase (ALP) Staining

ALP staining was performed using a commercial ALP kit (Sigma) according to the manufacturer's instruction. Images of ALP-positive cells were recorded using HP Scanjet G4010. In addition, bight field images were obtained using an Olympus microscope (IX51, Olympus, Japan).

Example 7: Embryoid Body Differentiation

In order to measure the potential of hESC differentiation, human embryoid bodies (hEBs) were cultured in hEB medium (DMEM/F12 containing 10% serum replacement) in non-tissue culture treated Petri dishes. After 5 days of growth in suspension, the embryoid bodies were transferred to gelatin-coated plates and cultured in hEBs. The cells attached to the bottom of the plate were allowed to stand under the above-described conditions for 15 days so as to differentiate while replacing the medium, if necessary.

Example 8: Immunocytochemistry

For immunostaining, cells were seeded on Matrigel-coated 4-well Lab-Tek chamber slides (Nunc, Naperville, Ill.) and cultured for 5 days under the indicated conditions. The cells were fixed in 4% paraformaldehyde at room temperature for 15 minutes, and then washed with PBS/0.2% BSA. Next, the cells were passed through PBS/0.2% BSA/0.1% Triton X-100 for 15 minutes, and then incubated with 4% normal donkey serum (Molecular Probes, Eugene, Oreg., USA) in PBS/0.2% BSA at room temperature for 1 hour. The cells were diluted with PBS/0.2% BSA, and then reacted with primary antibody at 4° C. for 2 hours. After washing, the cells were reacted with FITC- or Alexa594-conjugated secondary antibody (Invitrogen) in PBS/0.2% BSA at room temperature for 1 hour. The cells were counterstained with 10 μg/ml DAPI. The chamber slide was observed with an Olympus microscope or an Axiovert 200M microscope (Carl Zeiss, Gottingen, Germany).

Example 9: Analysis of Promoter Methylation of Reprogramming Transcription Factors In order to verify the characteristics of human embryonic stem cells and induced pluripotent stem cells established using gene-transfected retrovirus, promoter methylation of Oct3/4 and Nanog that are human embryonic stem cell-specific transcription factors was analyzed. To extract genomic DNA, reprogrammed stem cells and human embryonic stem cells, cultured in human embryonic stem cell media for 6 days, were extracted using a DNA extraction kit (Qiagen Genomic DNA purification kit). Bisulfite sequencing was performed in three steps. In the first step, DNA was modified using sodium bisulfite, and in the second step, the gene region (generally promoter region) to be analyzed was amplified by PCR, and in the third step, the PCR product was sequenced to determine the degree of methylation of DNA. The DNA modification process using sodium bisulfite was performed using commercial EZ DNA Methylation Kit (Zymo Research). When DNA is treated with bisulfite, methylated cytosine does not change, whereas unmethylated cytosine is converted into uracil. Thus, when DNA is amplified by PCR using primers specific for the nucleotide sequences of cytosine and uracil, methylated DNA and unmethylated DNA can be distinguished from each other. The primers used are shown in Table 1 below.

TABLE 1

| Gene | Primer (Forward) | Primer (Reverse) | Accession No. |
|---|---|---|---|
| For bisulfate sequencing | | | |
| bi Oct4-1 | ATTTGTTTTTTGGGTAGTTAAAGGT (SEQ ID NO: 1) | CCAACTATCTTCATCTTAATA ACATCC (SEQ ID NO: 2) | NM_002701 |
| bi Oct4-2 | GGATGTTATTAAGATGAAGATAGTTGG (SEQ ID NO: 3) | CCTAAACTCCCCTTCAAAATC TATT (SEQ ID NO: 4) | NM_002701 |
| bi Nanog | TGGTTAGGTTGGTTTTAAATTTTTG (SEQ ID NO: 5) | AACCCACCCTTATAAATTCTC AATTA (SEQ ID NO: 6) | NM_024865 |

The PCR reaction mix consisted of 1 μg bisulfite-treated DNA, 0.25 mM/l dNTP, 1.5 mM/l MgCl2, 50 pM primer, 1×PCR buffer and 2.5U Platinum Taq DNA polymerase (Invitrogen, Carlsbad, Calif., USA) and had a final volume of 20 μl. The PCR reaction was performed under the following conditions: initial denaturation at 95° C. for 10 min, and then 40 cycles, each consisting of 95° C. for 1 min, 60° C. for 1 min and 72° C. for 1 min, followed by final extension at 72° C. for 10 min. The PCR reaction product was electrophoresed on 1.5% agarose gel, and after gel electrophoresis, it was cloned into a pCR2.1-TOPO vector (Invitrogen). The nucleotide sequences of methylated and unmethylated DNAs were analyzed by sequencing using a M13 primer pair.

Example 10: Karyotype Analysis

Cultured human reprogrammed stem cells were analyzed by G-banding. A representative image was obtained using ChIPS-Karyo (Chromosome Image Processing System, GenDix).

Figure 1B:
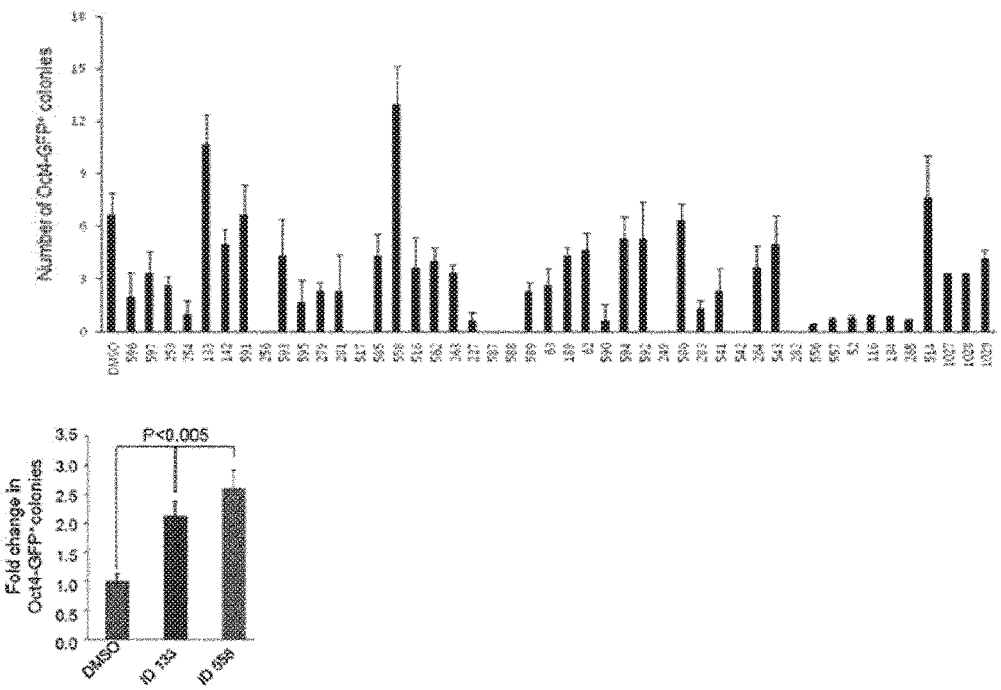

Example 11: Screening of Reprogramming Stimulating Compound (RSC) 133 that is Novel Low-Molecular-Weight Compound that Increases the Efficiency of Reprogramming of Mouse and Human Cells 11-1. Discovery of Mouse Cell Reprogramming Factor by Analog Library Screening of Novel Trans-3-Indoleacrylic Acid-Based Compounds To discover low-molecular-weight compounds that are involved in the reprogramming process, analog library screening of novel trans-3-indoleacrylic acid-based compounds was performed in mouse cells. Mouse embryonic fibroblasts (OG2-MEF: hemizygous for the Oct4-GFP transgene) were transfected with reprogramming viruses of Oct4, Sox2, Klf4 and c-Myc (OSKM), and after 5 days, the cells were seeded on gelatin-coated 12-well plates and incubated with mouse embryonic stem cell culture medium containing each of low-molecular-weight compounds until colonies having a morphology similar to that mouse stem cells were formed so that endogenous Oct4 GFP fluorescence was expressed (FIG. 1A). After 15 days, the number of colonies expressing endogenous Oct4 GFP fluorescence was measured to examine compounds that increased the efficiency of reprogramming compared to that of the control group, and as a result, it was shown that RSC-133 and ID-558 among the screened compounds showed the effect of increasing the efficiency of reprogramming (FIG. 1B). Based on the results of the primary screening, novel indole-acrylic acid/indole-propionic acid derivatives (reaction scheme 1) were prepared, and structure-activity relationship (SAR) for the reprogramming efficiency of the produced compounds was evaluated. It was found that, among the candidate compounds tested, indole-acrylic acid derivative compounds RSC-133 and ID-558 comprising an amino-free indole ring coupled to a benzoic acid derivative by a double bond showed the high reprogramming efficiency. In the benzoic acid derivative portion of the two compounds, RSC-133 comprises simple benzamide, and ID-558 comprises 4-hydroxy-N,N-dimethylbenzamide.

Figure 2A:
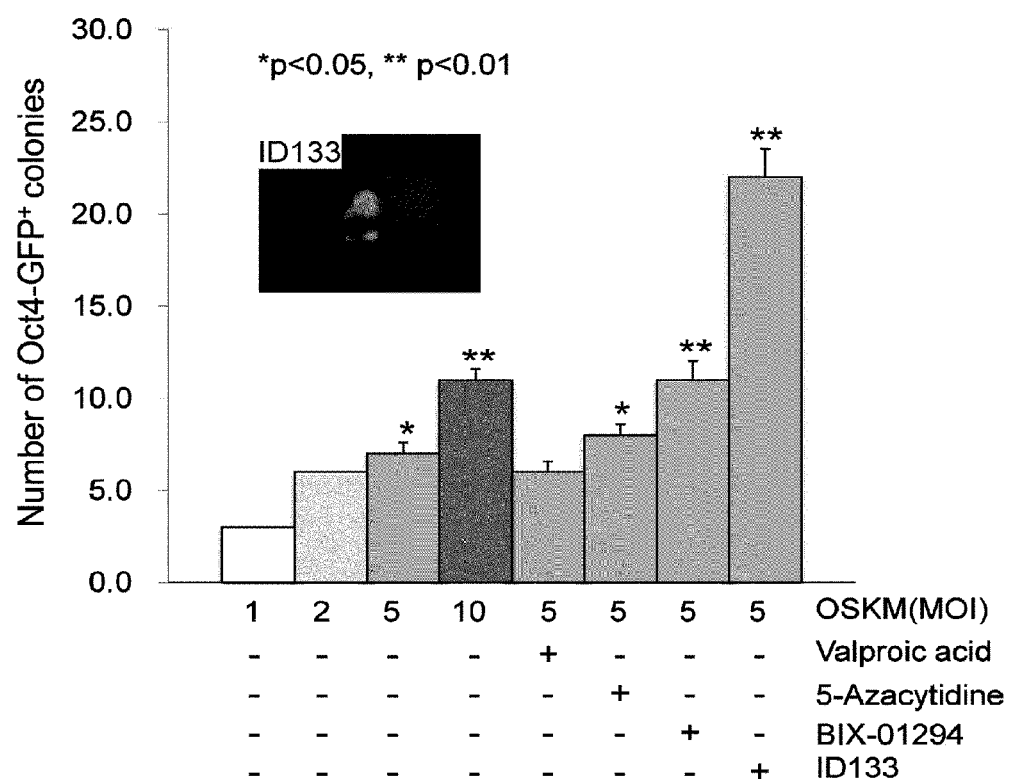
FIG. 2a shows the results of comparatively analyzing the increase in reprogramming efficiency caused by the novel low-molecular-weight compound 133. The reprogramming-promoting effects of a DNA methyltransferase inhibitor (5-Azacytidine; AZA), a G9a histone methyltransferase inhibitor (BIX-01294) and a histone deacetylase inhibitor (Valproic acid; VPA), which are low-molecular-weight compounds reported to promote the production of reprogrammed stem cells, and the novel low-molecular-weight 133, were comparatively analyzed by measuring the number of colonies expressing endogenous Oct4 GFP fluorescence. Treatment with RSC-133 greatly increased the efficiency of reprogramming compared to control group or treatment with other compounds or reprogramming of induction of reprogramming viruses (Oct4, Sox2, Klf4, and c-Myc (OSKM)). The values shown on the graph are mean values. The data are expressed as mean±SD (n=3) (**P<0.05).
Figure 2B:
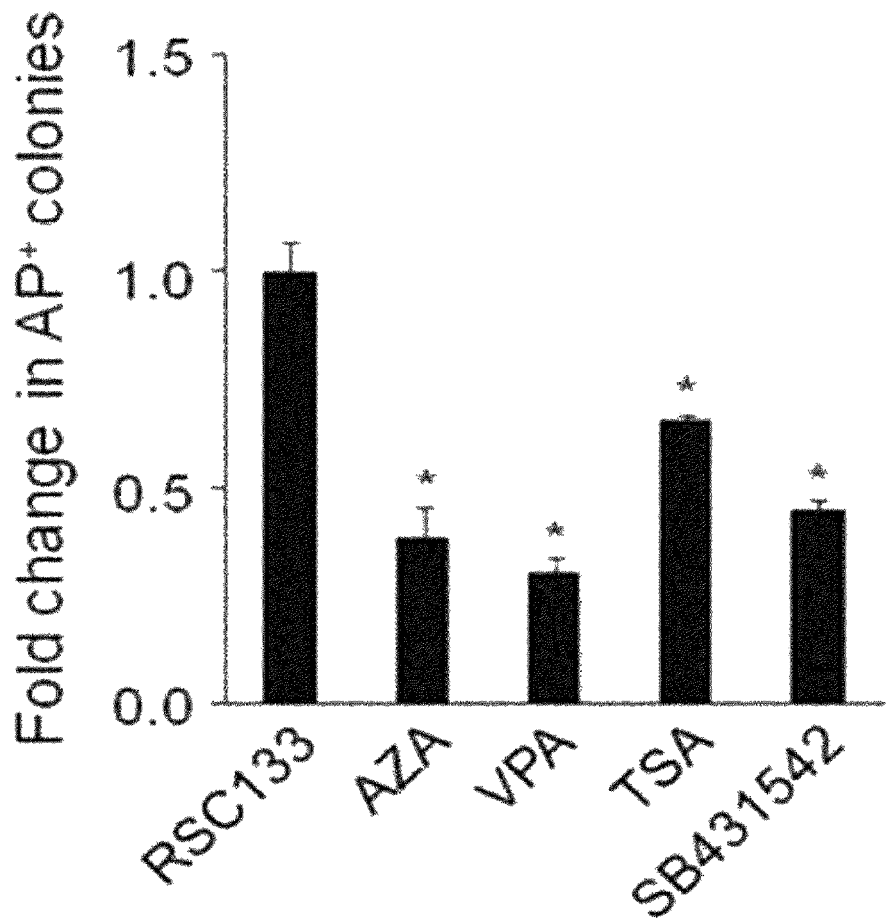
FIG. 2b shows the results of comparatively analyzing the increase in reprogramming efficiency caused by the novel low-molecular-weight compound 133. In a process of inducing the reprogramming of human skin fibroblasts by insertion of an OSKM reprogramming factor, the cells were treated with AZA (0.5 μM), VPA (1 mM), TSA (20 nM), SB431542 (10 μM) and RSC 133 (10 μM), and the number of AP-positive colonies was counted to measure the efficiency of reprogramming. The values shown on the graph are mean values. The data are expressed as mean±SD (n=3).

According to previous reports, a DNA methyltransferase inhibitor (5-Azacytidine), a G9a histone methyltransferase inhibitor (BIX-01294) and a histone deacetylase inhibitor (Valproic acid; VPA), which are low-molecular-weight compounds, are known to promote the production of reprogrammed stem cells. Interestingly, treatment with the novel low-molecular-weight compound RSC-133 greatly increased the efficiency of reprogramming compared to treatment with the reported compounds or compared to when increasing the MOI value of OSKM reprogramming virus (FIG. 2a). The effect of RSC-133 on the promotion of reprogramming of human cells was 1.5-3.3 times higher than those of AZA, VPA, TSA and SB431542 that are compounds known to promote the production of iPSC (FIG. 2b).

Figure 3:
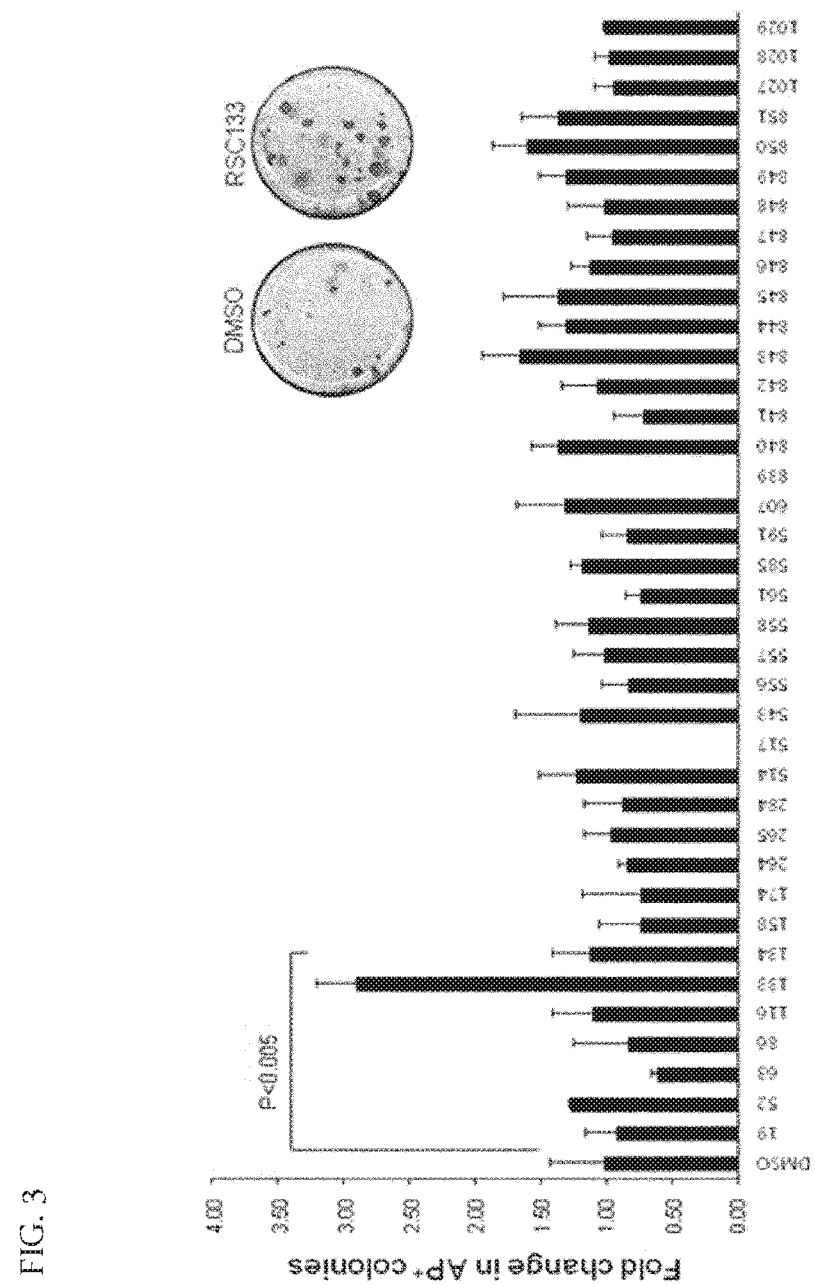
FIG. 3 shows the results of screening reprogramming factors of human skin fibroblasts (hFFs) using analog library screening of novel trans-3-indoleacrylic acid-based compounds. In order to screen low-molecular-weight compounds that promote the production of reprogrammed stem cells, human fibroblasts were transduced with reprogramming viruses (Oct4, Sox2, Klf4, and c-Myc). After 5 days, the cells were seeded on Matrigel-coated plates, and then cultured in MEF-conditioned medium (CM) containing each of low-molecular-weight compounds until colonies having a morphology similar to that of human embryonic stem cells were formed. After 15 days, alkaline phosphatase (AP) activity was measured, and compounds that increased the efficiency of reprogramming compared to that of a control group were selected. RSC-133 increased the efficiency of reprogramming of human skin fibroblasts, similar to that of mouse embryonic fibroblasts. The values shown on the graph are mean values. The data are expressed as mean±SD (n=3).

11-2. Discovery of Reprogramming Regulators of Human Cells by Analog Library Screening of Novel Trans-3-Indoleacrylic Acid-Based Compounds To discover low-molecular-weight compounds that involved in the reprogramming of human somatic cells, reprogramming regulators of human skin fibroblasts were investigated by analog library screening of thirty selected novel trans-3-indoleacrylic acid-based compounds. Human skin fibroblasts were transfected with OSKM reprogramming virus, and after 5 days, the cells were seeded on Matrigel-coated 12-well plates and incubated in MEF-conditioned medium (CM) containing each of the low-molecular-weight compounds until colonies having a morphology similar to that of human embryonic stem cells were formed. After 15 days, alkaline phosphatase (AP) activity was measured to determine compounds that increased the efficiency of reprogramming compared to that of the control group, and as a result, it was found that RSC-133 increased the efficiency of reprogramming of human skin fibroblasts, similar to that of mouse embryonic fibroblasts (FIG. 3).

11-3. Examination of Effect of Novel Low-Molecular-Weight Compound 133 on Increase in Efficiency of Reprogramming of Human Skin Fibroblasts The novel low-molecular-weight compound 133 showed the effect of increasing the efficiency of reprogramming of human skin fibroblasts not only in normal conditions (21% $O_2$), but also hypoxic conditions (5% $O_2$), compared to the control group (FIG. 4). The efficiency of reprogramming increases in hypoxic conditions (5% $O_2$), and the novel compound 133 could exhibit a synergistic effect in the reprogramming process stimulated by such hypoxic conditions (5% $O_2$) (FIG. 4A) and could form reprogrammed stem cell colonies (FIG. 4B).

Figure 5:
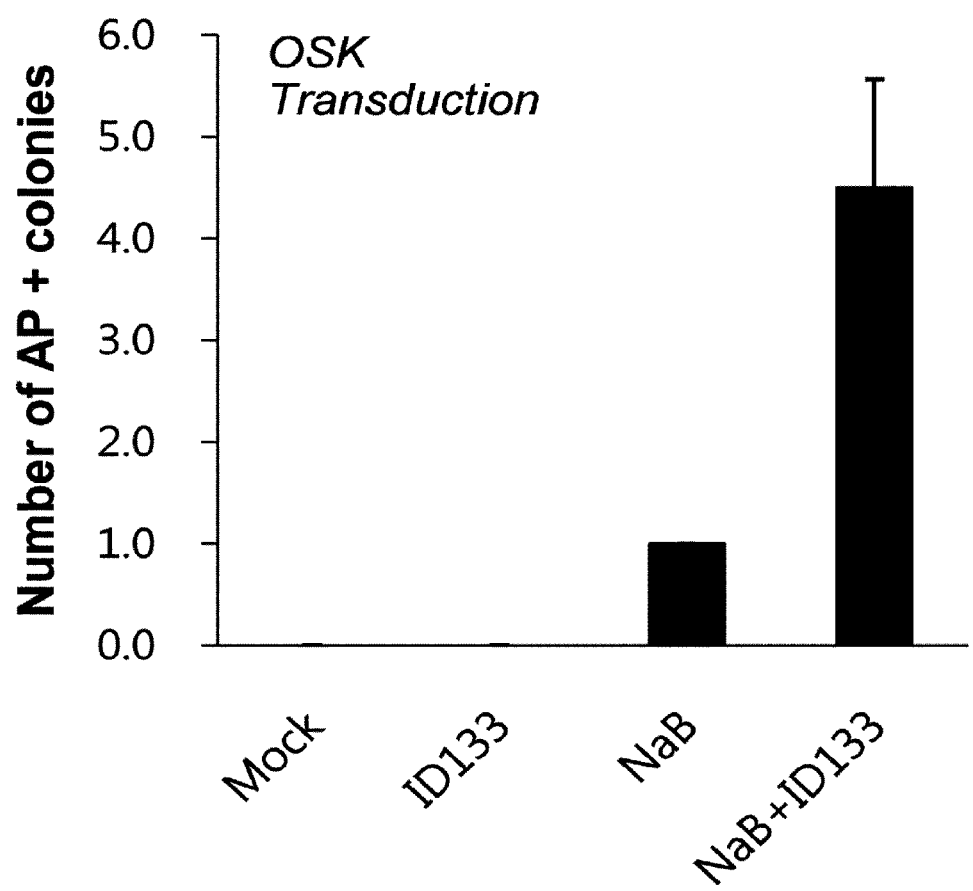
FIG. 5 shows the results of examining whether the novel low-molecular-weight compound 133 shows the effect of substituting for an existing reprogramming factor (c-Myc) when the generation of reprogrammed stem cells from human skin fibroblasts is induced by addition of the novel low-molecular-weight compound 133. The compound RSC-133 alone did not show the substituting effect, but addition of the compound RSC-133 in combination with sodium butyrate (NaB) substituted for the c-Myc factor to increase the efficiency of reprogramming compared to that of a control group. The efficiency of reprogramming obtained by measuring the number of AP-positive colonies is graphically shown. The values shown on the graph are mean values. The data are expressed as mean±SD (n=3). The values shown on the graph are mean values.

Meanwhile, examination was carried out to determine whether the novel low-molecular-weight compound 133 can substitute for an existing reprogramming factor (c-Myc) when the reprogramming of human skin fibroblasts is induced by the addition of the compound 133. It is known that c-Myc is an oncogene and the re-expression of c-Myc virus gene in reprogrammed stem cells formed after induction of reprogramming is involved in carcinogenesis. For this reason, studies on reprogramming methods excluding c-Myc have received attention. Interestingly, RSC-133 alone did not show the substituting effect, but the addition of RSC-133 in combination with sodium butyrate (NaB) substituted for c-Myc factor to increase the efficiency of reprogramming compared to that of the control group (FIG. 5). In conclusion, it was found that the novel low-molecular-weight compound RSC-133 is a factor that increases the efficiency of reprogramming of mouse and human cells.

Figure 8:
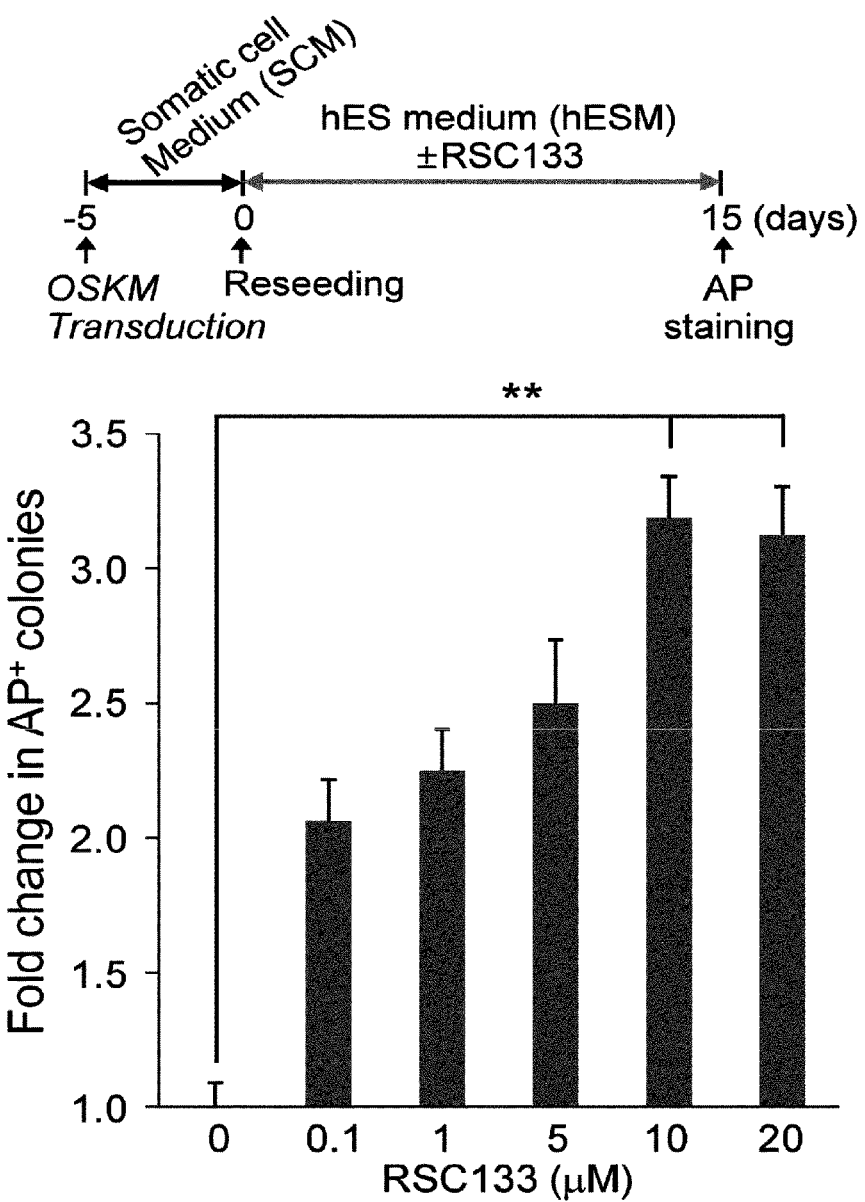
FIG. 8 shows that RSC-133 increased the efficiency of reprogramming in a manner dependent on the concentration thereof in a culture medium for reprogramming. The upper panel schematically shows the experimental process. The lower panel is a graph showing the efficiency of reprogramming obtained by measuring the number AP-positive colonies as a function of the concentration of RSC-133 treated. The values shown on the graph are mean values. The data are expressed as mean±SD (n=3) (**P<0.005, by t-test).
Figure 9:
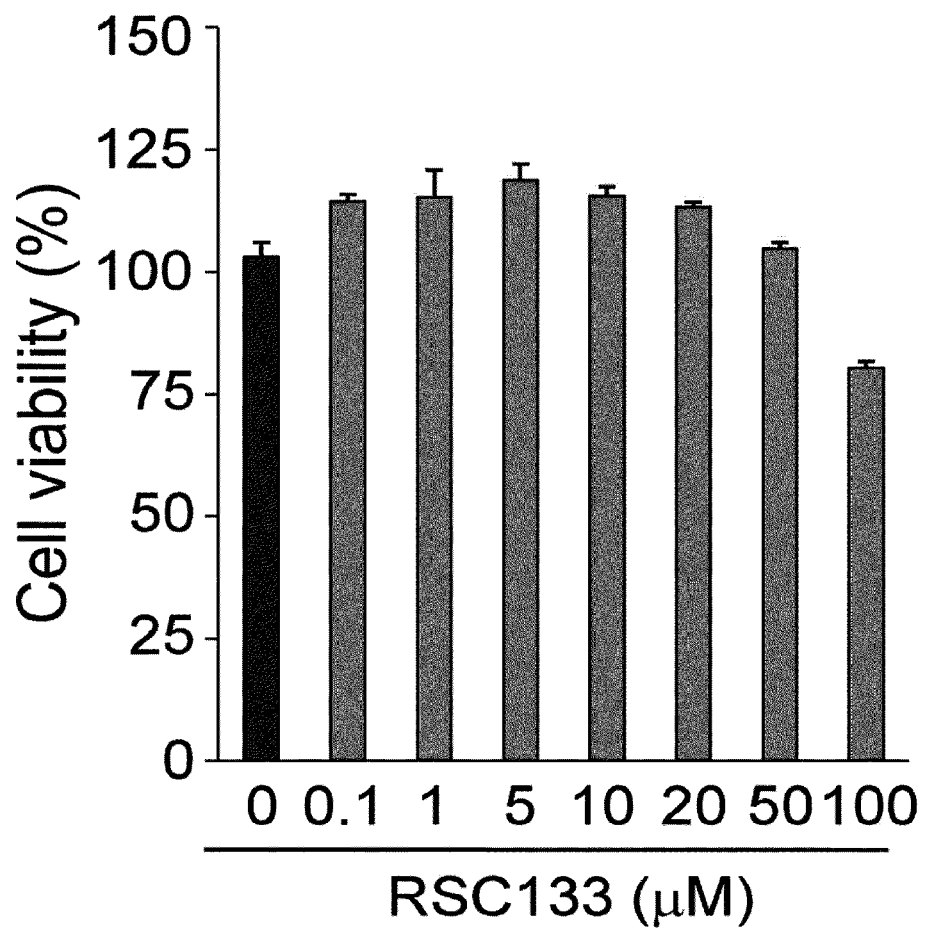
FIG. 9 is a graph showing the results of analyzing the effect of RSC-133 on the cytotoxicity of human skin fibroblasts. At 72 hours after treatment with various concentrations of RSC-133, cytotoxicity was measured by MTT (3-(4,5-dimethylthiazol-2-yl)-2,5-diphenyltetrazolium bromide (yellow tetrazole) assays. The values shown on the graph are mean values. The data are expressed as mean±SD (n=3).

Example 12: Examination of Effect of Reprogramming Factor RSC-133 on Concentration-Dependent Induction of Reprogramming Whether the effect of RSC-133 on the increase in the efficiency of reprogramming is dependent on the amount of RSC-133 added was examined. Specifically, human skin fibroblasts were transfected with OSKM virus, and then, according to the experimental method shown in FIG. 8, whether RSC-133 increases the efficiency of reprogramming in a manner dependent on the concentration thereof in a culture medium for reprogramming was examined. The efficiency of reprogramming was determined by measuring the number of colonies showing AP activity. As a result, it could be seen that RSC-133 could increase the efficiency of reprogramming in a concentration-dependent manner at a treatment concentration of up to 10 µM (FIG. 8). The reason why the efficiency of reprogramming did not increase at 20 µM is not that a high concentration of RSC-133 induces the cytotoxicity of human skin fibroblasts (FIG. 9). Thus, it can be seen that 10 µM of RSC-133 can increase the efficiency of reprogramming of human skin fibroblasts to the highest level.

Example 13: Examination of Reprogramming Process in which RSC-133 is Involved and Establishment of Efficient Reprogramming Using the Same In order to examine the role of RSC-133 that is involved in the reprogramming process of human skin fibroblasts, RSC-133 was added during different periods of time in the reprogramming process as shown in the left panel of FIG. 10. The efficiency of reprogramming was determined by counting the number of colonies showing AP activity. As a result, when the cells were treated with RSC-133 for the same period of time (5, 10 and 15 days) and when the cells were treated with RSC-133 in the initial stage (including 5 days after viral infection) of the reprogramming process, the efficiency of reprogramming could be significantly increased compared to those in other periods of time. However, when treatment with RSC-133 was continuously performed throughout the reprogramming process, the efficiency of reprogramming was increased to the highest level (condition 1 in FIG. 10). Thus, it can be seen that, although RSC-133 is involved in the initial stage of reprogramming, continuous treatment with RSC-133 increases the efficiency of reprogramming to the highest level, suggesting that RSC-133 is involved not only in the induction of reprogramming, but also in the maintenance of reprogrammed stem cells.

Example 14: Effect of RSC-133 on Promotion of Cell Growth

Figure 11:
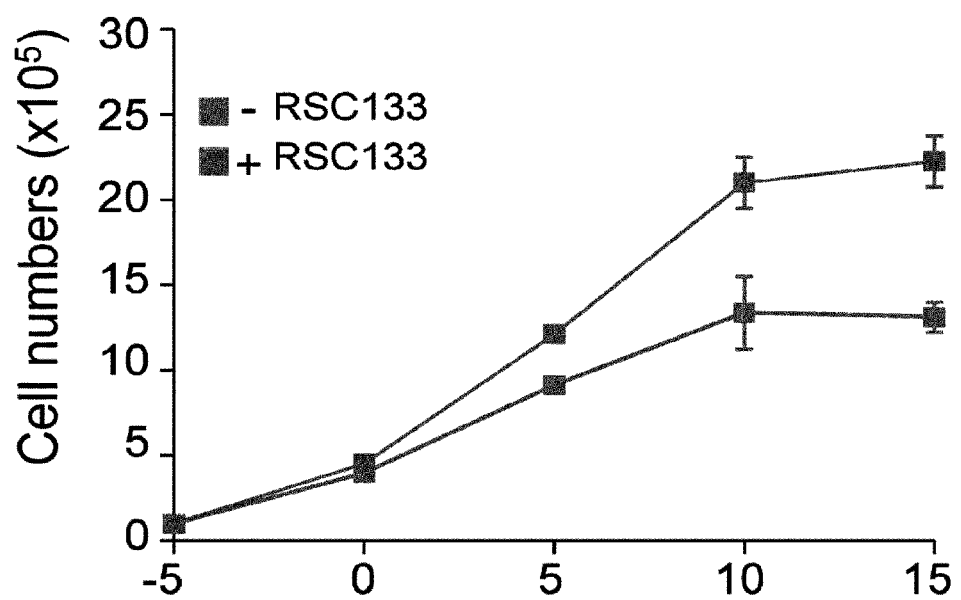
FIG. 11 is a graph showing the effect of RSC-133 on cell growth during a reprogramming process. The results were obtained in the same manner as those in FIG. 10. The values shown on the graph are mean values. The data are are expressed as mean±SD (n=3).
Figure 12:
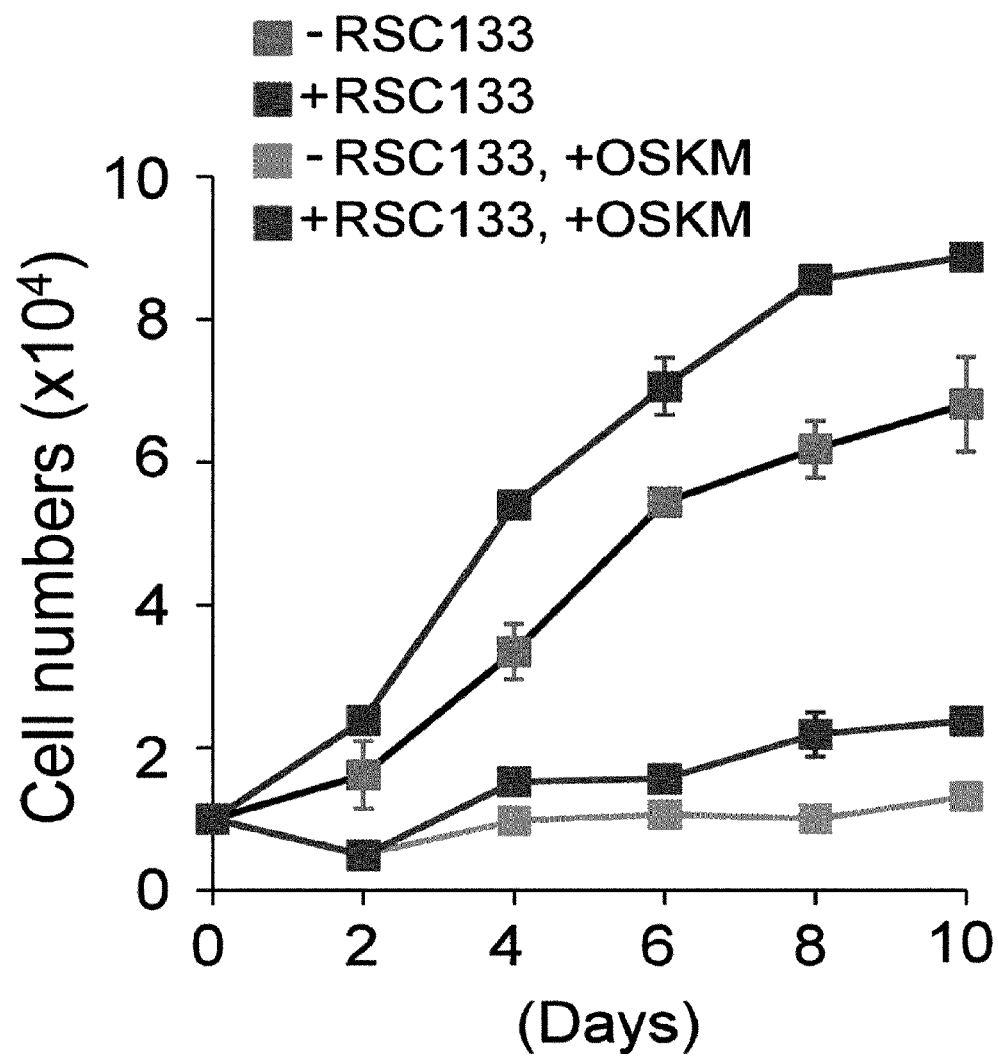
FIG. 12 is a graph showing the results of examining the effect of RSC-133 on the growth of human skin fibroblasts or human skin fibroblasts infected with a reprogramming factor (OSKM) virus. The values shown on the graph are mean values. The data are mean±SD (n=3).
Figure 13:
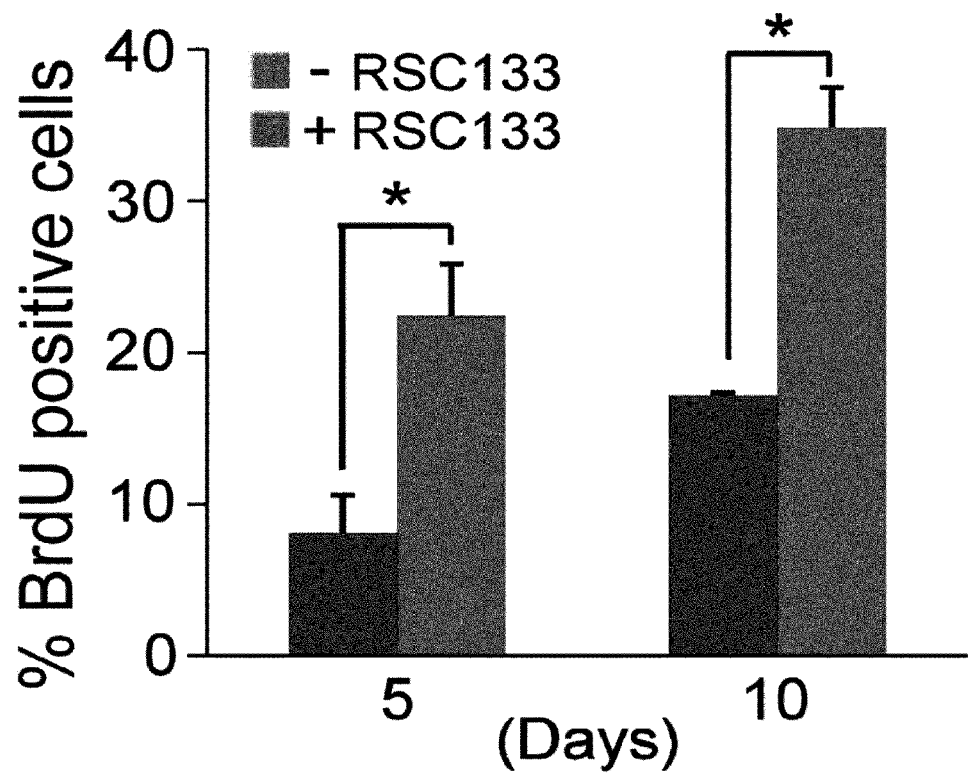
FIG. 13 shows that RSC-133 increased proliferating cell population during a reprogramming process. Immunocytochemical analysis was performed using monoclonal antibody for bromodeoxyuridine (BrdU), and then percent BrdU positive cells are graphically shown. The values shown on the graph are mean values. The data are expressed as ±SD (n=3) (*P<0.05, by t-test).
Figure 14:
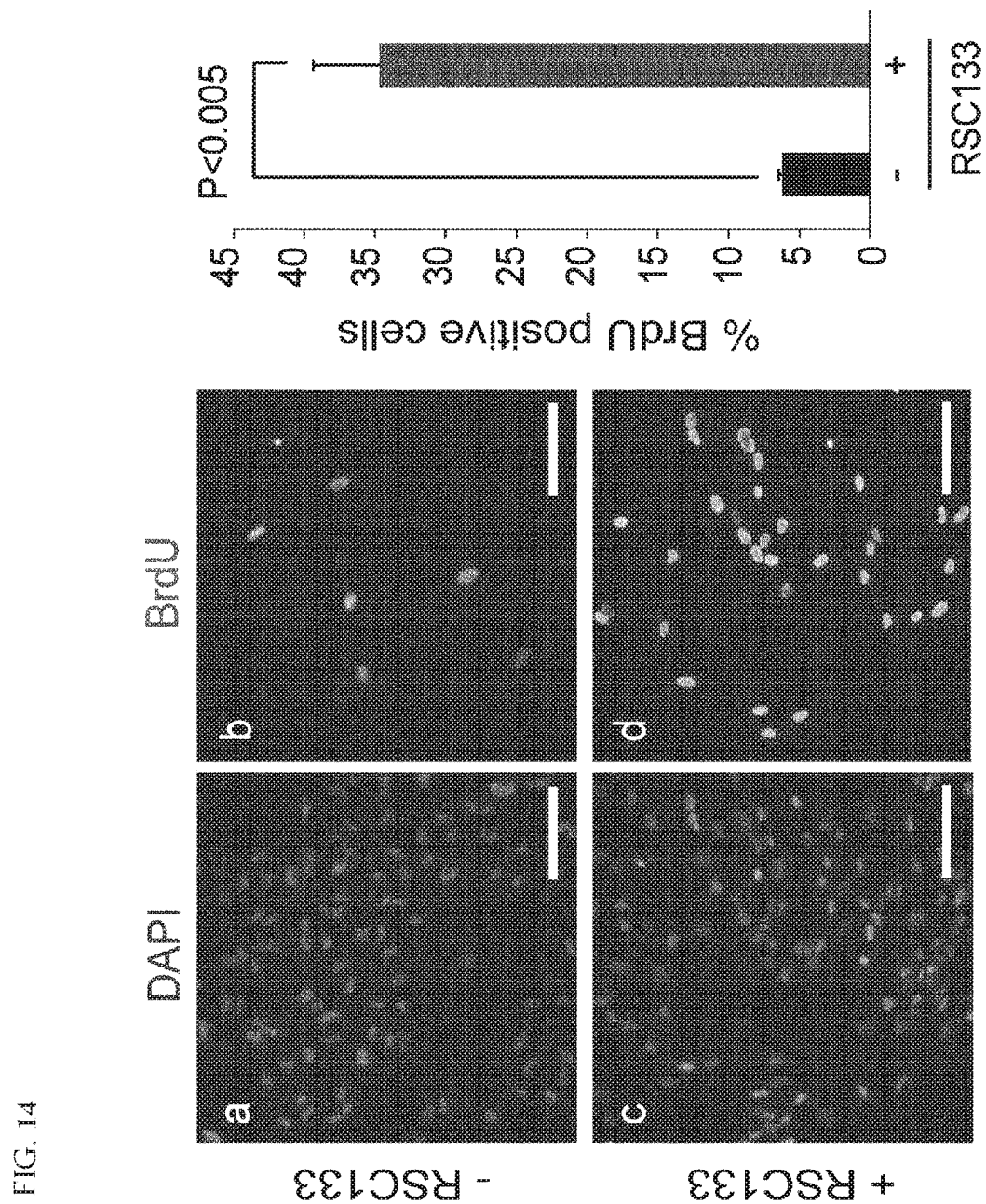
FIG. 14 shows that RSC-133 increased proliferating cell population in human skin fibroblasts infected with reprogramming factor (OSKM) virus. The left panel is a set of graphs showing the results of immunocytochemical analysis performed using monoclonal antibody for BrdU, and the right panel is a graph showing the results of measurement of percent BrdU positive cells. The values shown on the graph are mean values. The data are expressed as mean±SD (n=3).
Figure 16:
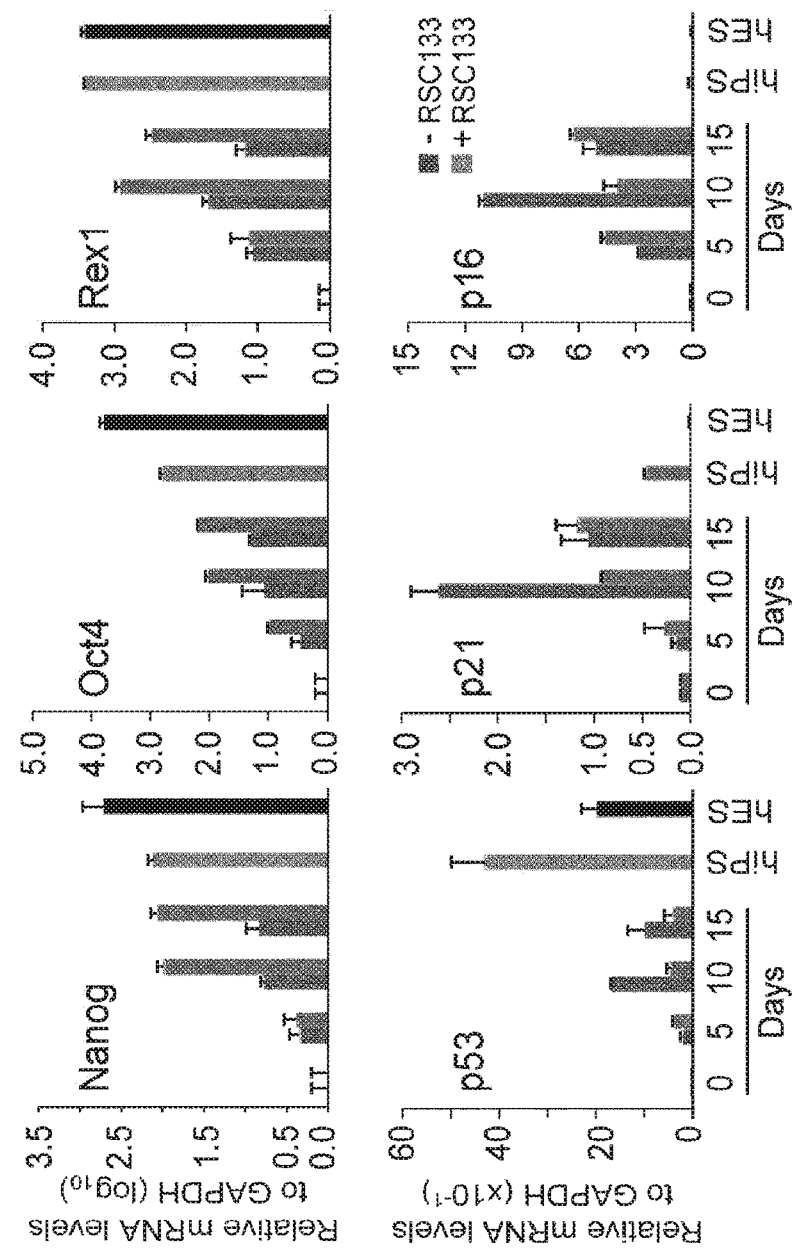
FIG. 16 shows the results of examining the effect of RSC-133 on a reprogramming process. The relative expression levels of mRNA during a reprogramming process were measured, and as a result, it was shown that, in a test group whose reprogramming was induced by treatment with RSC-133, the expressions of the pluripotency-specific markers Nanog, Oct4 and Rex1 were relatively increased, and the expressions of p53, p21 and p16 known to inhibit reprogramming were relatively inhibited.

Recent reports indicated that the promotion of cell growth leads to an increase in the efficiency of reprogramming. In addition, the growth rate of cells is associated with the self-renewal ability of embryonic stem cells. Thus, whether the novel compound RSC-133 can promote cell growth during reprogramming was examined. As a result, it could be seen that when reprogramming was induced while the cells were treated with RSC-133, the growth rate of the cells increased by about 1,7 times compared to that of the control group (FIG. 11). In addition, even when reprogramming was not induced, RSC-133 showed a function of increasing the growth rate of human skin fibroblasts (FIG. 12). In other words, in human skin fibroblasts or human skin fibroblasts which were transfected with reprogramming factor (OSKM) virus but the reprogramming of which was not induced, treatment with RSC-133 increased the growth of the cells (FIG. 12). Meanwhile, whether RSC-133 can increase proliferating cell population was examined by immunocytochemical analysis using a monoclonal antibody for bromodeoxyuridine (BrdU). The results of the analysis indicated that, during the reprogramming process (FIGS. 13 and 16) and in human skin fibroblasts which were transfected with reprogramming factor (OSKM) virus but the reprogramming of which was not induced (FIG. 14), treatment with RSC-133 increased BrdU-positive cell population. This suggests that RSC-133 can promote cell growth to increase the efficiency of reprogramming.

Example 15: Examination of Reprogramming Process Stimulated by RSC-133

Figure 10:
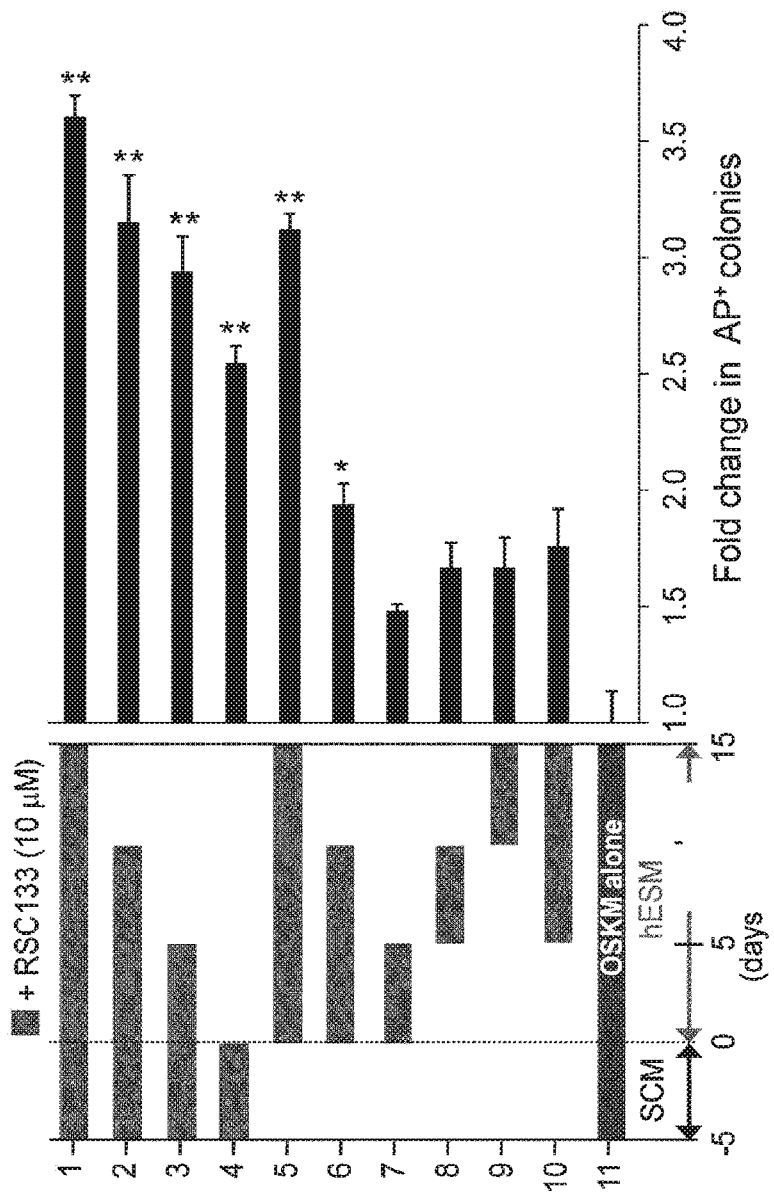
FIG. 10 shows the results of examining a reprogramming process, in which RSC-133 is involved, and an efficient reprogramming method utilizing the same. The left panel schematically shows the experimental process. The right panel shows the reprogramming efficiency measured by counting the number of AP-positive colonies after addition of RSC-133 during different periods of time in the reprogramming process. The values shown on the graph are mean values. The data are expressed as mean±SD (n=3) (*P<0.05, **P<0.005, by t-test).
Figure 15:
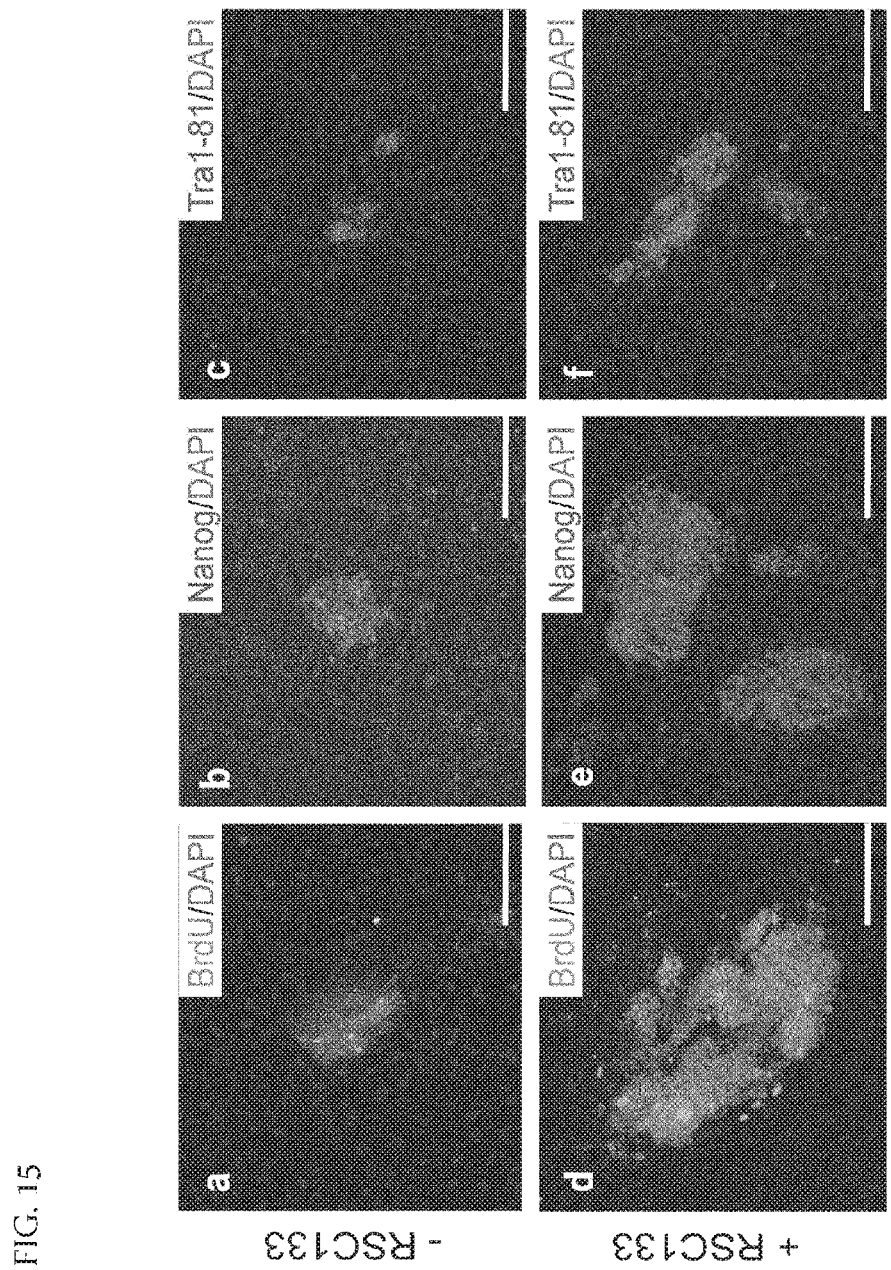
FIG. 15 is a set of photographs showing the results of immunocytochemical analysis performed using monoclonal antibodies for BrdU and undifferentiation markers (Nanog and Tra1-81) in cells cultured in the presence or absence of RSC-133. After induction of reprogramming, human skin fibroblasts were cultured for 10 days in the presence or absence of RSC-133, followed by immunocytochemical analysis (scale bar=200 μm).
Figure 17:
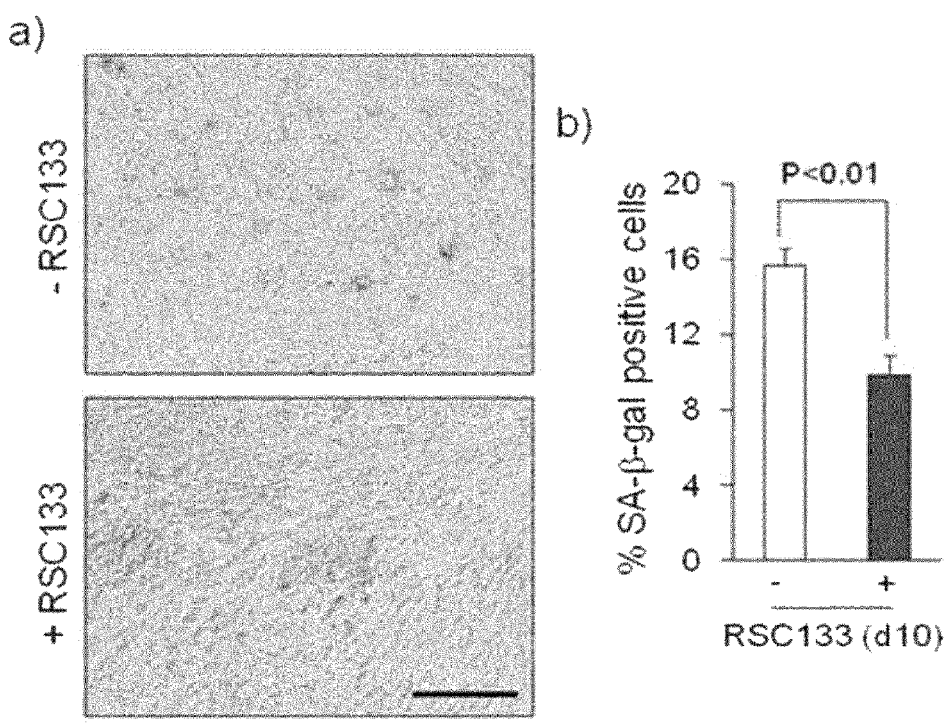
FIG. 17 shows the results of examining the effect of RSC-133 on cell cycle arrest (cell aging) in a reprogramming process. The degree of cell cycle arrest during a reprogramming process was measured by the measurement of SA-β-Gal, and as a result, it was shown that cell cycle arrest was relatively reduced in a test group whose reprogramming was induced by treatment with RSC-133. The values shown on the graph are mean values. The data are expressed as mean±SD (scale bar=200 μm, **P<0.01).

In order to examine whether RSC-133 can increase the rate of reprogramming, the relative levels of mRNA expressed during the reprogramming process were measured. Specifically, according to the experimental method as shown in FIG. 10, human skin fibroblasts were transfected with OSKM virus, and then the cells were harvested at 5-day intervals, and the expression levels of genes in the cells cultured in the presence or absence of RSC-133 were analyzed by real-time RT-PCR. As a result, it was shown that, in the test group treated with RSC-133 to induce reprogramming, the expression levels of the undifferentiation markers Nanog, Oct4 and Rex1 were relatively increased (FIG. 15 and the upper panel of FIG. 16), and the expression levels of p53, p21 and p16 known to be involved in a reprogramming inhibitory mechanisms were relatively inhibited (the lower panel of FIG. 16). In addition, at 10 days after induction of reprogramming, the ratio of cellular senescence-related β-galactosidase (SA-β-gal)-positive cells decreased by 37.23% compared to that of an untreated control group (OSKM alone) (FIG. 17). Thus, it can be seen that RSC-133 can increase the efficiency of reprogramming and also can be involved in the reprogramming process to stimulate kinetics.

Figure 18:
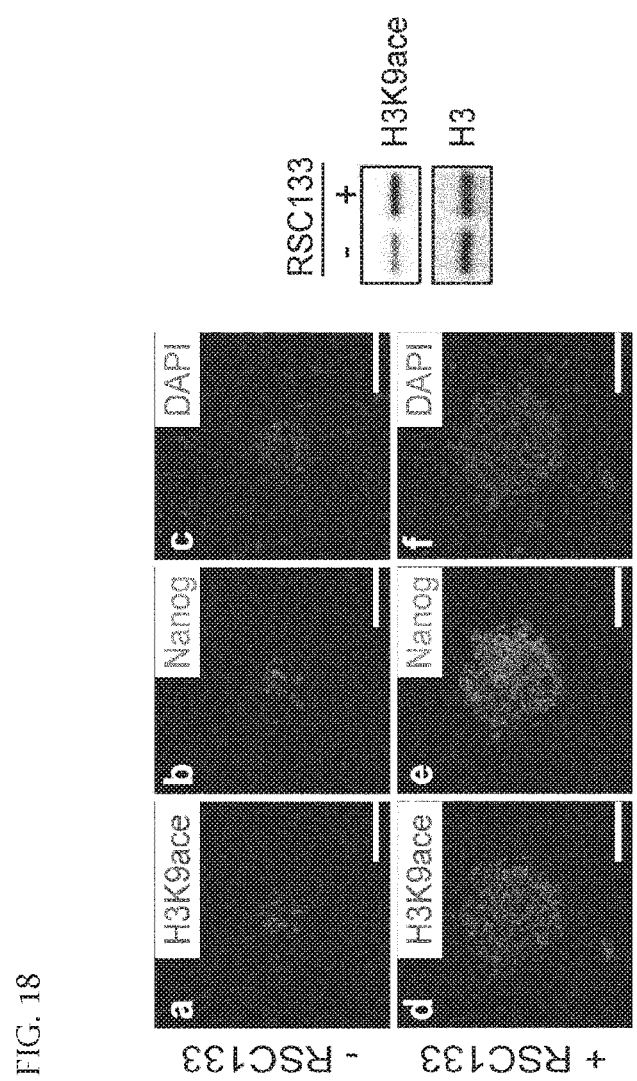
FIG. 18 shows the effect of RSC-133 on histone acetylation (H3K9ace) during a reprogramming process. The left panel is a set of photographs showing the results obtained by inducing the reprogramming of human skin fibroblasts, culturing the cells for 10 days in the presence or absence of RSC-133, and then analyzing the cells by immunocytochemistry using monoclonal antibodies for H3K9ace and an undifferentiation marker (Nanog) (scale bar=200 μm). The right panel shows the results of measuring the level of H3K9ace by Western blot analysis. H3 protein was used as an internal control.

Example 16: Analysis of Function of RSC-133 that is Involved in Histone Acetylation During Reprogramming Most of various low-molecular-weight compounds known to be involved in the reprogramming process are involved genome methylation patterns, histone acetylation patterns or major signaling mechanisms. Among them, histone deacetylase (HDAC) inhibitors (VPA, TSA and SAHA) that are involved in the regulation of histone acetylation patterns are known to play an important role in the reprogramming process. Particularly, an increase in H3K9 acetylation (H3K9ace) levels is associated with pluripotency and reprogramming ability. As shown in FIG. 18, reprogramming of human skin fibroblasts was induced, and the cells were cultured for 10 days in the presence or absence of RSC-133, and then analyzed by immunocytochemistry using monoclonal antibodies for H3K9ace and an undifferentiation marker (Nanog), and as a result, the ratio of undifferentiated cells having a high H3K9ace level was higher in the test group treated with RSC-133 than in the control group (the left panel of FIG. 18). The same results were also obtained when the amount of protein was quantified by measuring the H3K9ace level by Western blot analysis (the right panel of FIG. 18).

Figure 19:
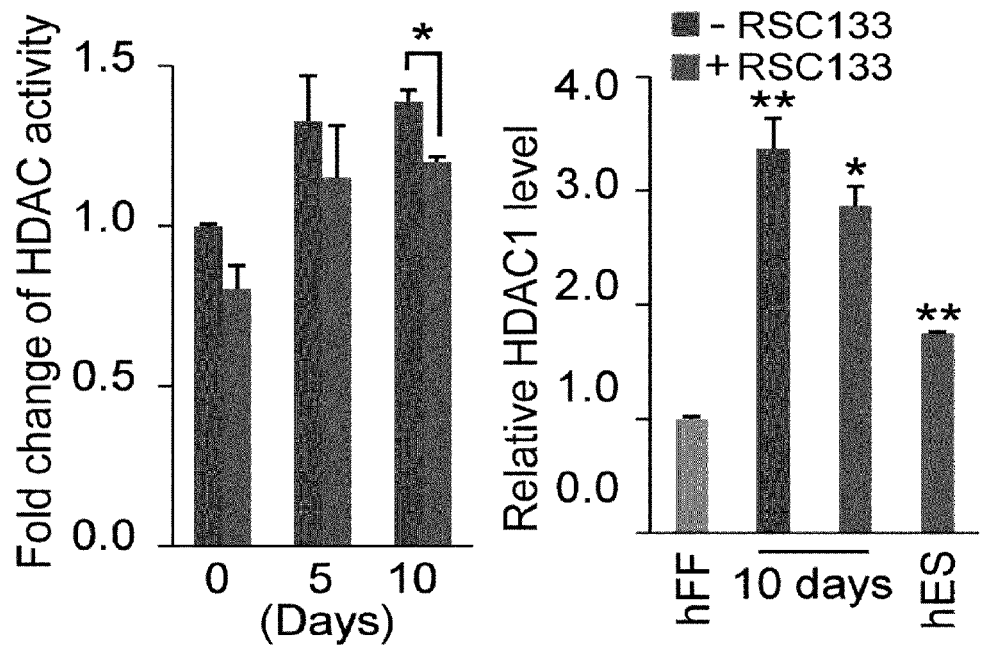
FIG. 19 shows the results of examining whether RSC-133 can inhibit histone deacetylase (HDAC) during the reprogramming of human skin fibroblasts. The left panel shows the results of measuring the activity of total HDAC enzymes during a reprogramming process performed in the presence or absence of RSC-133. The right panel shows the amount of HDAC1 protein measured after performing 10 days of culture in the presence or absence of RSC-133. The values shown on the graph are mean values. The data are expressed as mean±SD (n=3) (*P<0.01, **P<0.005, by t-test).

Next, whether the above-described results were results of the inhibition of HDAC enzyme by RSC-133 during reprogramming of human skin fibroblasts was examined. As a result, it could be seen that the activity of total HDAC enzymes was slightly inhibited by treatment with RSC-133 during reprogramming (the left panel of FIG. 19). According to the experimental method shown in FIG. 21, the expression levels of HDAC-family proteins were measured, and as a result, it could be seen that the expression level of HDAC1 in the test group treated with RSC-133 was inhibited at 10 days after treatment with RSC-133 compared to that of the control group (the light panel of FIG. 19 and FIG. 21). It was reported that HDAC1 can occupy the Oct4, Sox2, Klf4 and c-Myc gene loci in embryonic stem cells and that the expression of pluripotency-specific marker genes in HDAC1-deleted embryonic stem cells is increased. Thus, it is believed that RSC-133 can inhibit the function of HDAC1 and increase the H3K9ace level to stimulate the reprogramming process.

Figure 20:
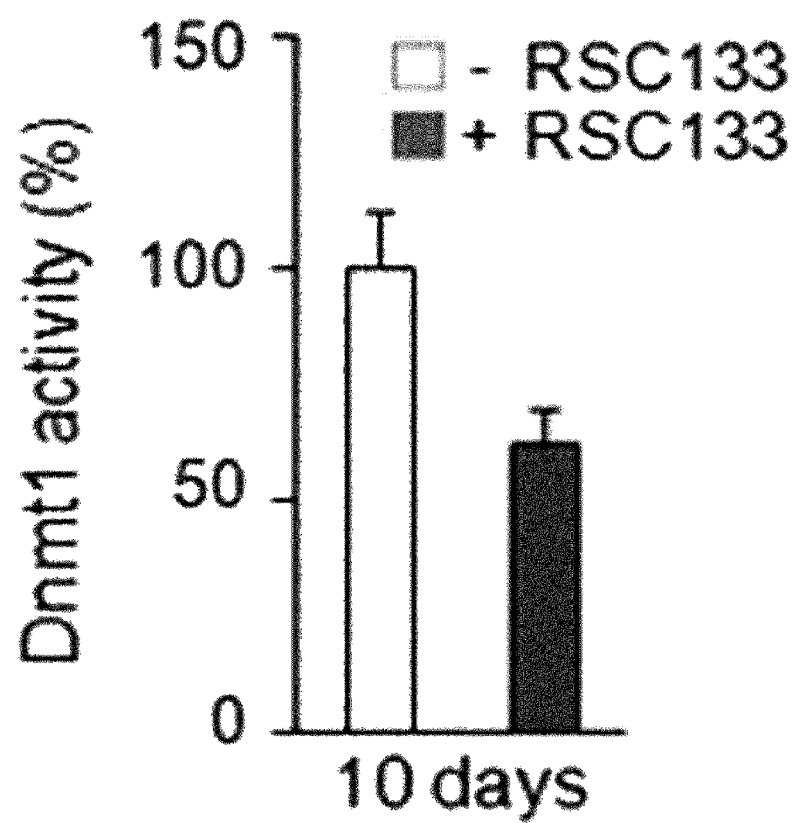
FIG. 20 shows the results of examining the effect of RSC-133 on the activity of DNA methyl transferase 1 (DNMT1) during the reprogramming of human skin fibroblasts. The graph shows the activity of DNMT1 measured after culturing human skin fibroblasts transduced with OSKM, for 10 days in the presence of RSC-133. For comparison, the activity of DNMT1 in the absence of RSC-133 was set at 100%.

Example 17: Analysis of Function of RSC-133 that is Involved in DNA Methylation During Reprogramming RSC133 regulates the activities of epigenetic regulators such as DNA methyltransferase (DNMT) and histone deacetylase (HDAC). At 10 days after induction of reprogramming by RSC133, the activity of DNMT1 was reduced by about 38% compared to that in an untreated control group (OSKM alone) (FIG. 20). Epigenetic chromatin remolding by DNA methylation and/or histone modification plays an important in a wide range of transcriptional regulation in the reprogramming process. When DNA methylation is inhibited by treatment with the DNA methylation inhibitor AZA or deletion of DNMT1, the conversion of the cells to iPSC is rapidly induced. The increased level of H3K9 histone acetylation (ace) is particularly associated with the restoration of pluripotency and reprogramming ability. It is known that DNA methylation by DNMT1 has a close connection with the change in chromatin status caused by HDAC activity. Putting these results together, it can be seen that the inhibition of DNMT1 and HDAC1 activity by RSC-133 changes DNA methylation and chromatin status and increases accessibility to the loci of above-defined four reprogramming enzymes to have an indirect effect on the transcriptional regulation of the genes, thereby promoting the reprogramming process.

Example 18: Analysis of Characteristics of Reprogrammed Human Stem Cells Induced by RSC-133

18-1. Analysis of Expression of Pluripotency-Specific Markers

Figure 22:
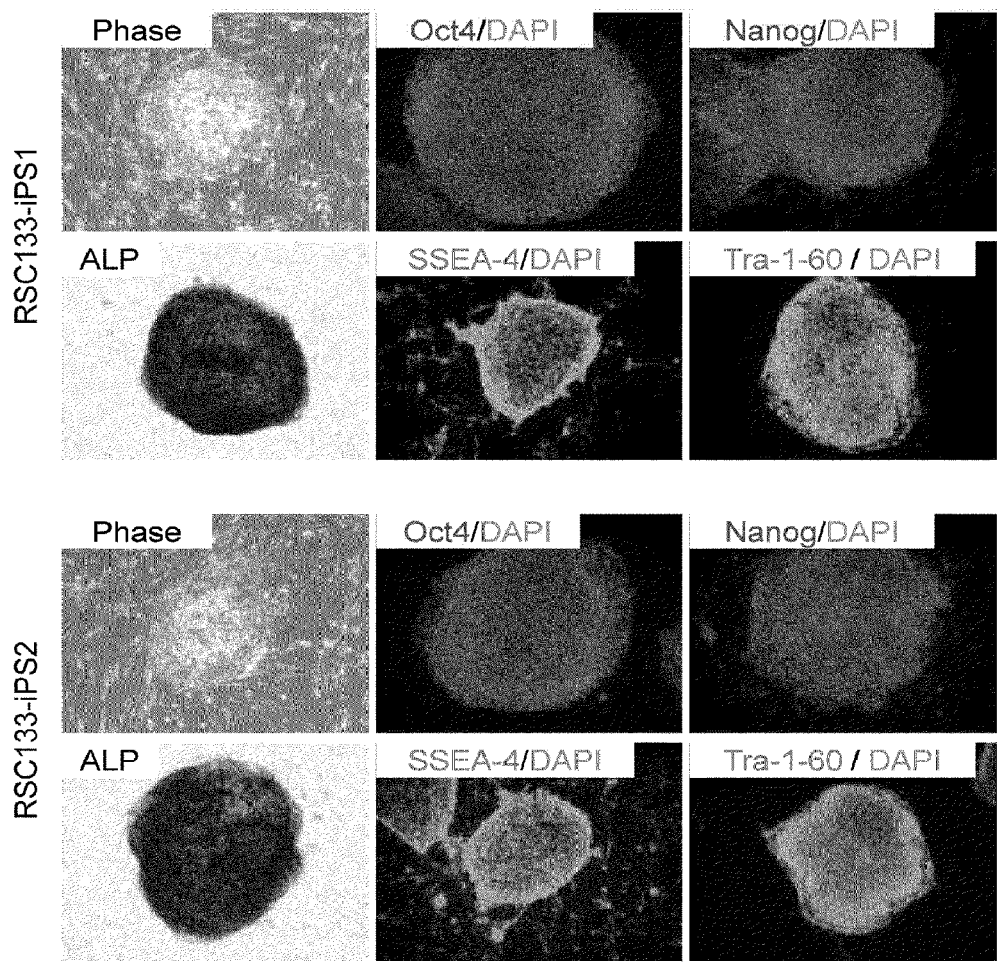
FIG. 22 shows the results of immunostaining performed to analyze the expression of pluripotency-specific markers in the reprogrammed stem cells (RSC133-iPS) reprogrammed from human skin fibroblasts by addition of RSC-133.
Figure 23:
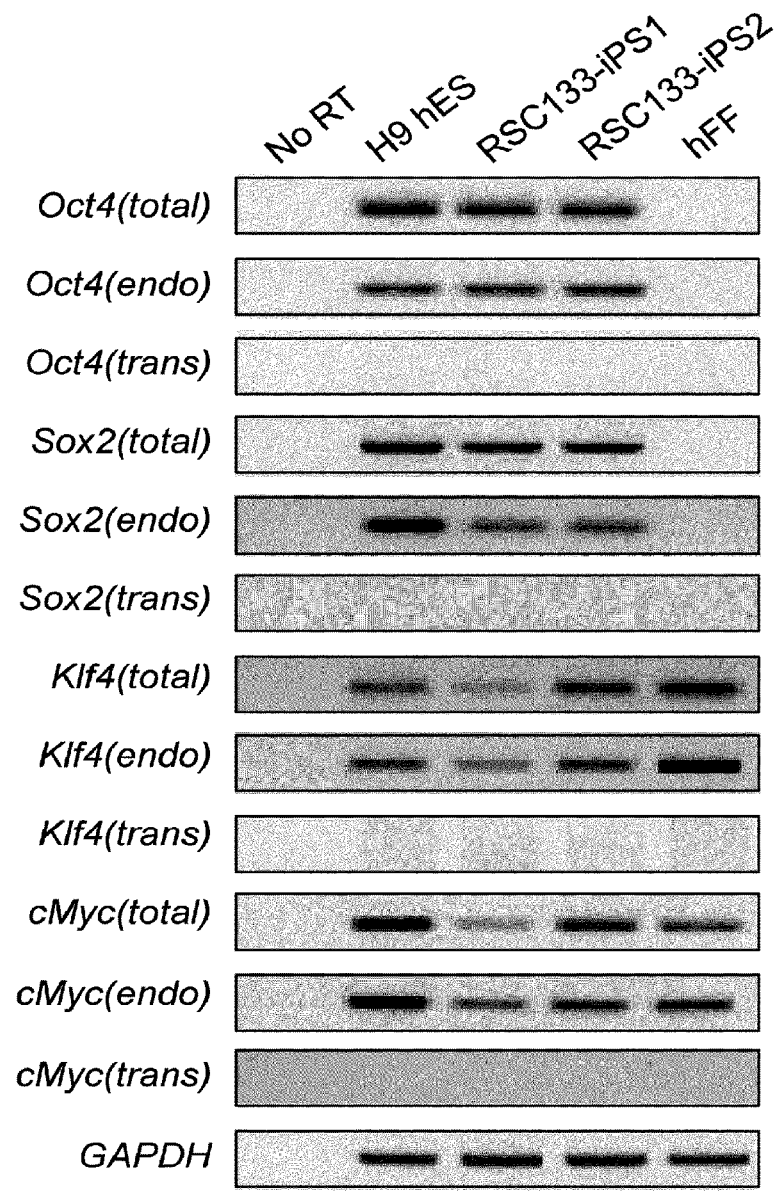
FIG. 23 shows the results of RT-PCR analysis performed to analyze the expressions of pluripotency-specific marker genes and reprogramming factors in reprogrammed stem cells (RSC133-iPS) induced from human skin fibroblasts by addition of RSC-133. Semi-quantitative RT-PCR was performed using transgene-specific PCR primers that can determine the relative expression between Total, Endo and retrovirus expression (Trans) genes.

The stem cell characteristics of the reprogrammed stem cell lines (RSC133-iPS) induced from human skin fibroblasts by the addition of RSC-133 were analyzed by ALP staining and immunostaining. Two cell lines (RSC133-iPS1 and RSC133-iPS2) were analyzed. As a result, the RSC133-iPS cell lines were very similar such that they were not distinguished morphologically or by the ALP staining and immunostaining of human embryonic stem cell markers (OCT4, NANOG, SSEA-3, SSEA-4, TRA-1-60, and TRA-1-81) (FIG. 22). In addition, the expressions of Oct4, Sox2, cMyc and Klf4 mRNA were analyzed by semi-quantitative RT-PCR, and as a result, it was shown that the RSC133-iPSs expressed Oct4, Sox2, cMyc and Klf4 at the total and endogenous levels similar to those in human embryonic stem cells and that the silencing of the genes introduced by retroviruses was completely completed (FIG. 23).

18-2. Analysis of Methylation in Reprogrammed Stem Cells Induced by RSC-133

Figure 21:
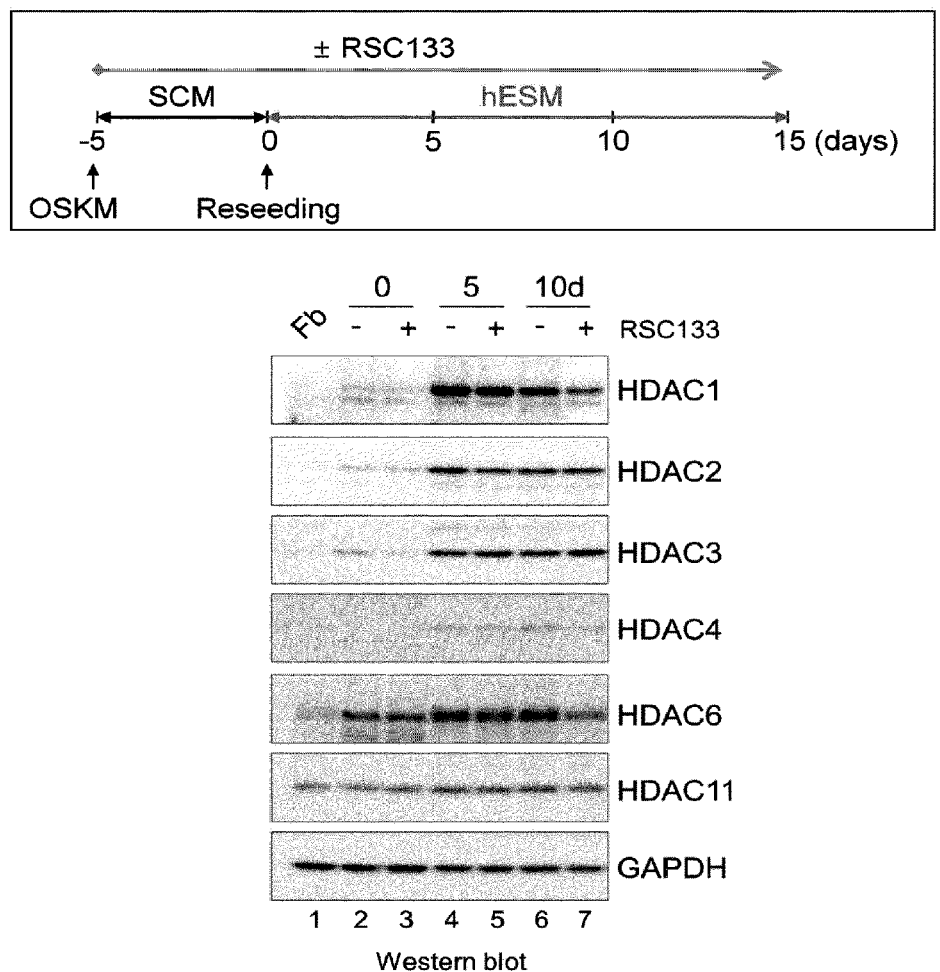
FIG. 21 shows the changes in amounts of HDAC-family proteins during the reprogramming of human skin fibroblasts in the presence or absence of RSC-133. The upper panel schematically shows an experimental process. The lower panel shows the results of measuring the changes in amounts of HDAC-family proteins by Western blot analysis. GAPDH protein was used as an internal control.
Figure 24:
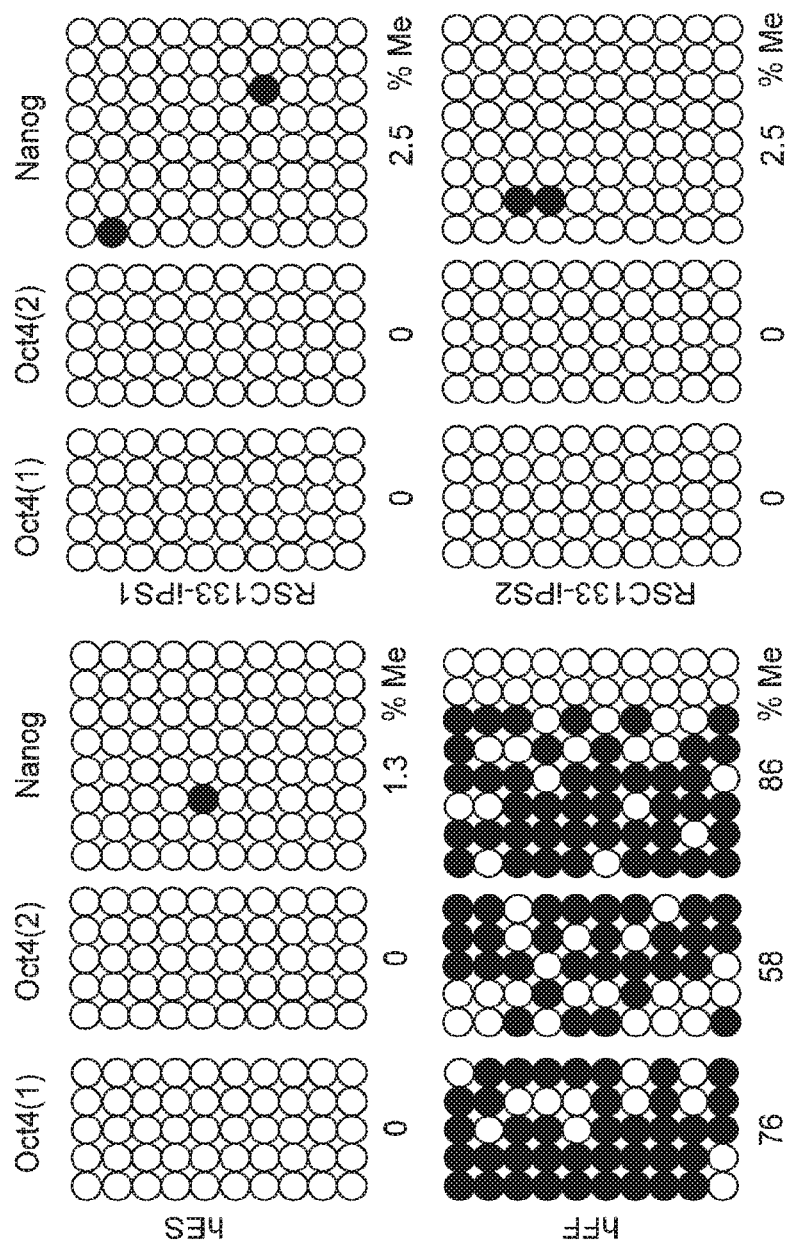
FIG. 24 shows the results of analyzing the promoter methylation patterns of Oct4 and Nanog transcription factors in the reprogrammed stem cells (RSC133-iPS) induced from human skin fibroblasts by addition of RSC-133, H9 human embryonic stem cells (hESs) and human skin somatic cells (hFFs) induced from human skin fibroblasts by addition of RSC-133. The horizontal row of circles indicates an individual sequence from one amplicon. The empty circles and the black circles indicate demethylated and methylated CpG, respectively, and the percentage (%) of methylated CpG is shown.

According to the method shown in Example 8, the degrees of the promoter methylation regions of the stem cell markers Oct4 and Nanog genes of the RSC133-iPSs were analyzed by bisulfite sequencing. As a result, as can be seen in FIG. 21, the RSC133-iPSs showed demethylation patterns similar to those of the human embryonic stem cells (H9), but the parent cells (hFFs) still maintained methylation (FIG. 24).

18-3. Analysis of Genomic Integration of Reprogrammed Stem Cells Induced by RSC-133

Figure 25:
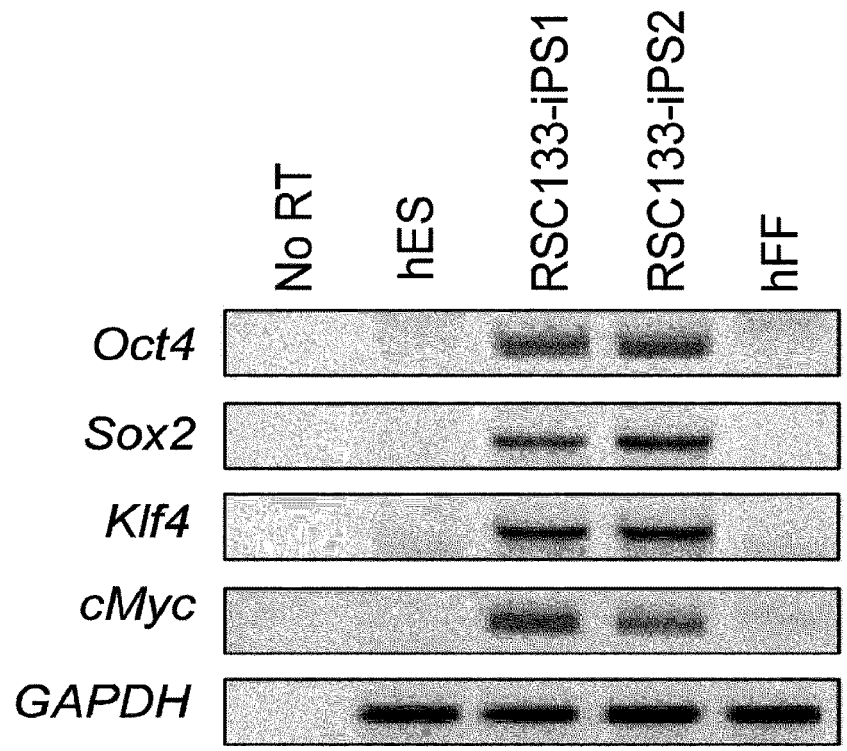
FIG. 25 shows the results of analyzing the integration of genes into the genome of reprogrammed stem cells (RSC133-iPS) reprogrammed from human skin fibroblasts by addition of RSC-133.

Genomic integration of each of RSC133-iPS1 and RSC133-iPS2 was analyzed. Specifically, genomic DNA was extracted from each of the cell lines using a DNeasy kit (Qiagen, Valencia, Calif.), and 300 ng of each of the genomic DNAs was amplified by PCR using primers capable of specifically amplifying the genomic DNA and the transferred gene. As a result, it was found that, in the RSC133-iPS cell lines, Oct4, Sox2, cMyc and Klf4 were integrated (FIG. 25). Herein, the human embryonic stem cell line (H9, hES) and the human skin fibroblast cell line (CRL2097, hFF) were used as control groups.

18-4. Analysis of Karyotype of Reprogrammed Stem Cells Induced by RSC-133

Figure 26:
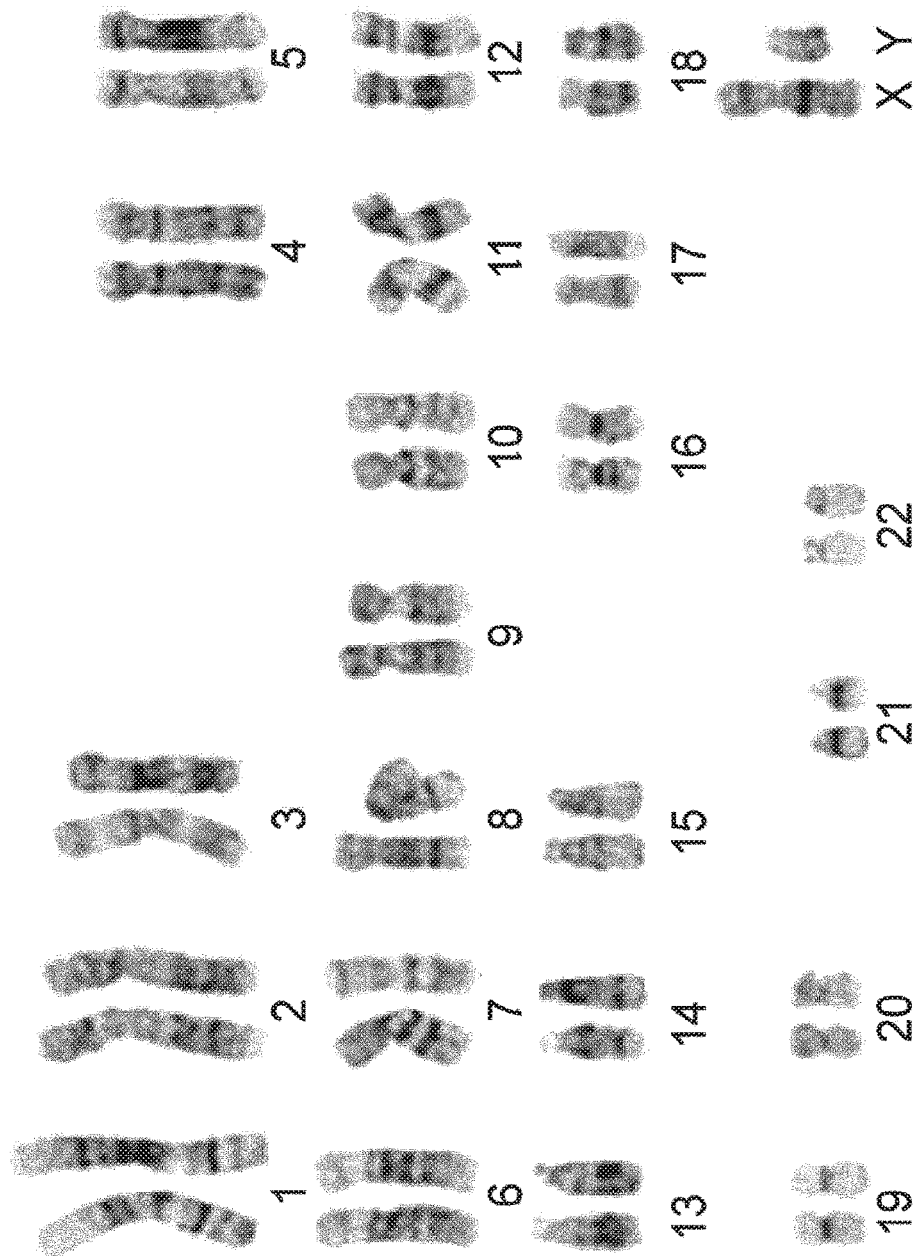
FIG. 26 shows that reprogrammed stem cells (RSC133-iPS) reprogrammed from human skin fibroblasts by addition of RSC-133 maintained a normal karyotype (46, XY).

The karyotype of the RSC133-iPSCs was analyzed by G-banding. Representative images were obtained using ChIPS-Karyo (Chromosome Image Processing System, GenDix) (FIG. 26). As a result, the reprogrammed RSC133-iPSCs showed a normal karyotype showed a normal karyotype (46, XY).

18-5. Examination of Pluripotent Ability of Reprogrammed Stem Cells Induced by RSC-133

In order to examine whether the reprogrammed stem cells (RSC133-iPS) from human fibroblasts by the addition of RSC-133 possess differentiation potential that is the feather of stem cells, the differentiation potential of embryoid bodies derived from each of the reprogrammed stem cell lines was examined. Specifically, the cells were cultured in suspension, and then the embryoid bodies were incubated again on gelatin-coated plates for 10 days under differentiation conditions, after which the expression of marker proteins that are expressed specifically in cells that differentiated into three germ layers was analyzed by immunochemical staining. As a result, cells positive to Tuj1 (exoderm), Nestin(exoderm), desmin (mesoderm), α-SMA (α-smooth muscle actin, mesoderm), Sox17 (endoderm) and FoxA2 (endoderm) were detected. Such results that the reprogrammed stem cells (RSC133-iPS) induced by RSC-133 had the capability to differentiate into three germ layers and maintained pluripotency.

Figure 27:
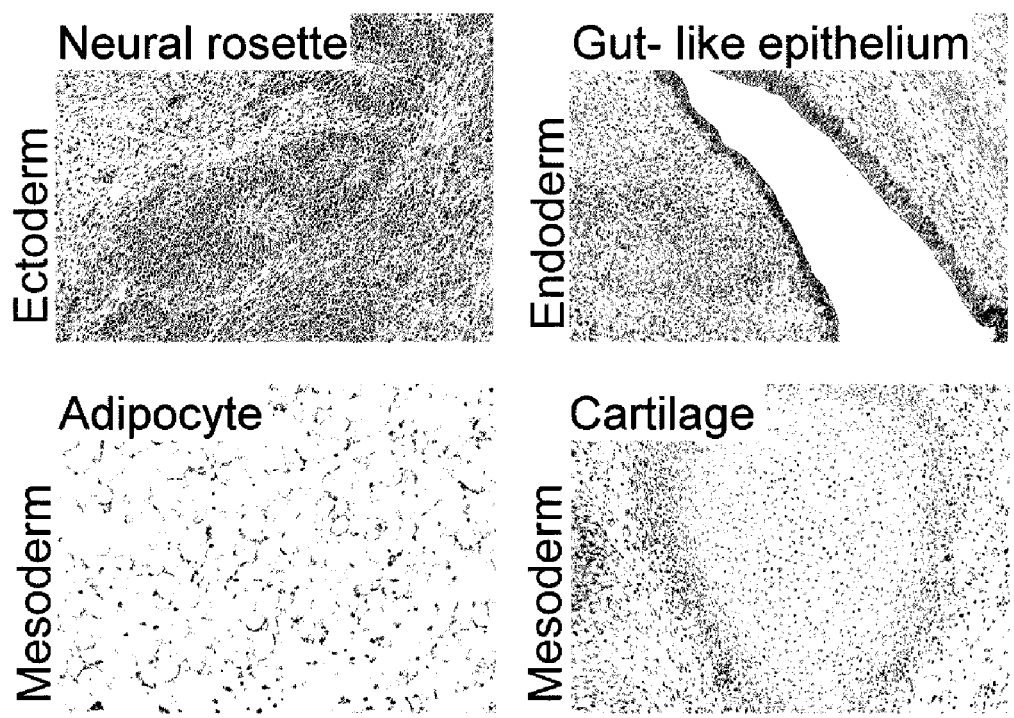
FIG. 27 is a set of photographs showing teratoma formation that demonstrates the in vivo differentiation potential of reprogrammed stem cells (RSC133-iPS) reprogrammed from human skin fibroblasts by addition of RSC-133.

In addition, in order to examine the in vivo pluripotency of the human reprogrammed stem cells (RSC133-iPS) induced by the addition of RSC-133, the reprogrammed stem cells RSC133-iPS were injected subcutaneously into the dorsal flanks of immunodeficiency (SCID) mice. After about 12 weeks, teratomas could be observed, and neural rosette (exoderm), adipocyte(mesoderm), cartilage (mesoderm) and gut-like epithelium (endoderm) were observed in the teratoma by hematoxylin/eosin staining (FIG. 27). This suggests that the human reprogrammed stem cells (RSC133-iPSCs) induced by the addition of RSC-133 have the capability to differentiate into three germ layers in vitro and in vivo.

Example 19. Effects of RSC-133 on Maintenance and Stimulation of Pluripotency

Figure 28:
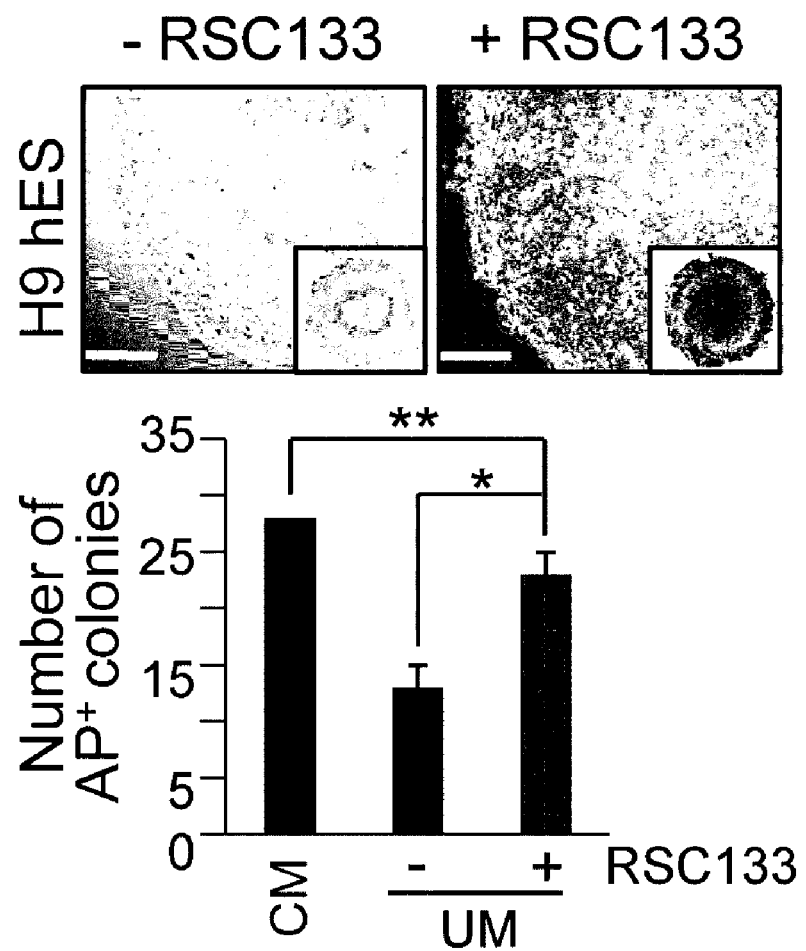
FIG. 28 shows the results of examining the function of RSC-133 that is involved in the acquisition of pluripotency. It was observed that, when H9 human embryonic stem cells (hESs) were cultured in unconditioned medium (UM), the differentiation thereof was induced, but when the cells were cultured in UM containing RSC-133, the degree of induced differentiation was inhibited, and pluripotency was acquired again. The efficiency of acquisition of pluripotency was measured by calculating the number of colonies showing AP activity. The values shown on the graph are mean values. The data are expressed as mean±SD (n=3) (*P<0.01, **P<0.005, by t-test).
Figure 29:
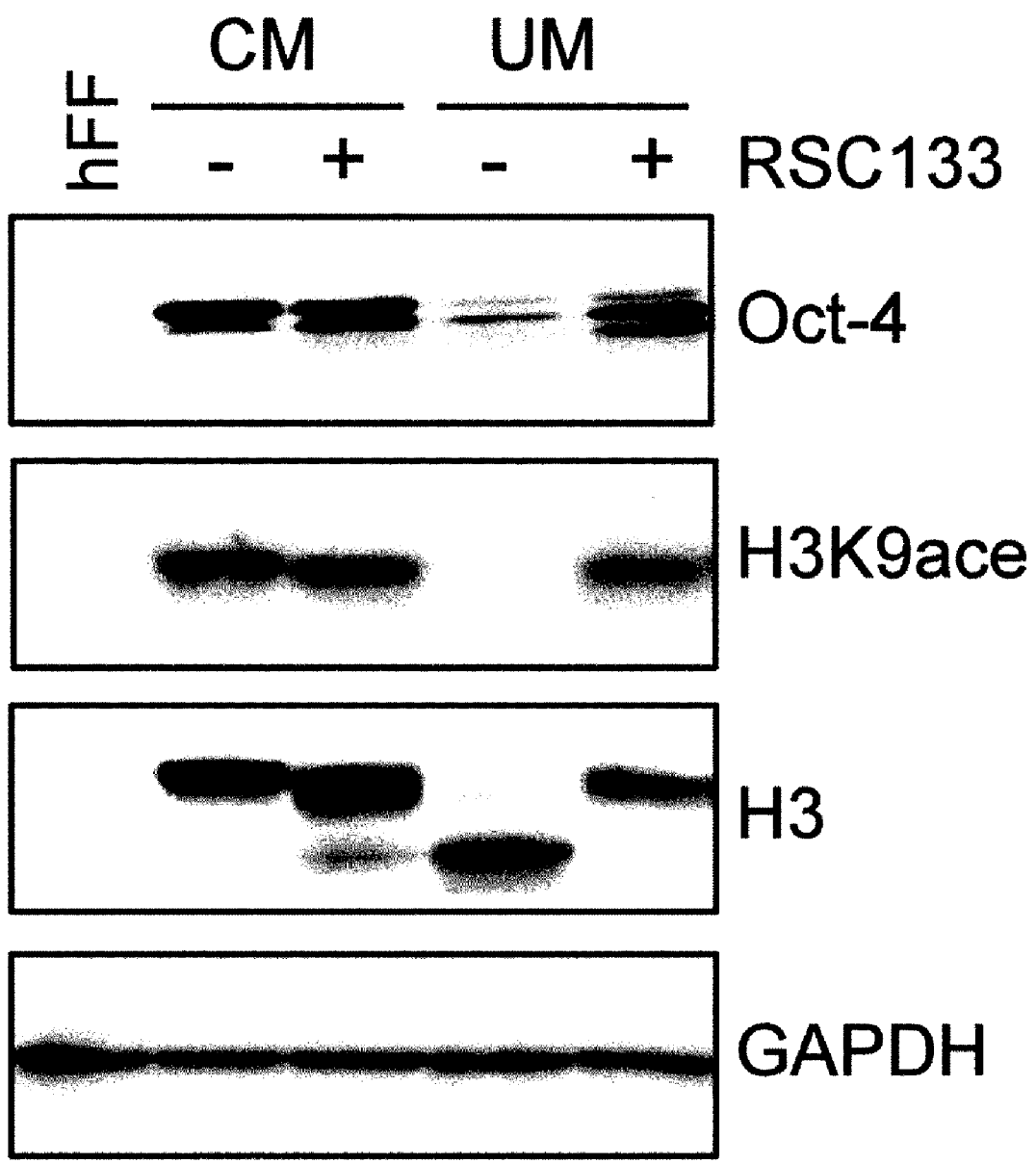
FIG. 29 shows the results of Western blot analysis performed to examine the change in amount of the pluripotency-specific markers Oct4 or H3K9ace in H9 human embryonic stem cells cultured in the presence or absence of RSC-133. Human skin fibroblasts (hFFs) were used as a negative control group. H3 and GAPDH proteins were used as internal controls.

When human embryonic stem cells (H9) are cultured in unconditioned medium (UM), their differentiation is induced. However, when the cells were cultured for 6 days in UM supplemented with RSC-133, it could be observed that the degree of induced differentiation was inhibited and pluripotency was re-acquired (the upper panel of FIG. 28). As a positive control group, embryonic stem cells cultured for 6 days in MEF-conditioned medium (CM) effective for maintenance of an undifferentiated state were used. The efficiency of maintenance of an undifferentiated state and inhibition of differentiation was determined by measuring the number of colonies showing AP activity (the lower panel of FIG. 28). In addition, the results of immunostaining at the protein level indicated that, when human embryonic stem cells were cultured in UM supplemented with RSC-133, the pluripotency-specific markers (Oct4 and Tra1-81) of the human embryonic stem cells were expressed at levels similar to those of human embryonic stem cells cultured in CM.

The inhibition of differentiation and maintenance of undifferentiation by RSC-133 was additionally verified by analysis of expression of the pluripotency-specific markers Oct4 and H3K9ace, and it was observed that the human embryonic stem cells cultured in UM containing RSC-133 expressed Oct4 and H3K9ace at levels similar to those in the human embryonic stem cells cultured in CM (FIG. 31). Thus, it was verified that RSC-133 has effects not only on the reprogramming of human somatic cells, but also on the maintenance of pluripotency of human pluripotent stem cells.

Although the preferred embodiments of the present invention have been described for illustrative purposes, those skilled in the art will appreciate that various modifications, additions and substitutions are possible, without departing from the scope and spirit of the invention as disclosed in the accompanying claims.

The invention claimed is:

1. A method of culturing pluripotent stem cells in an undifferentiated state, comprising a step of culturing the pluripotent stem cells in a medium comprising a compound of the following formula 1 or a pharmaceutically acceptable salt thereof:

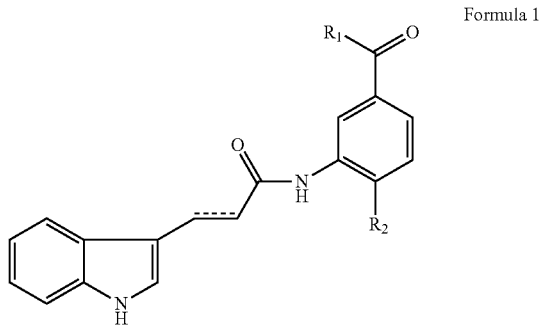

Formula 1 wherein (i) $R_1$ is an amino group ($NH_2$) and $R_2$ is hydrogen (H) or (ii) $R_1$ is a dimethylamino group ($N(CH_3)_2$) and $R_2$ is a hydroxyl group (OH; and a portion indicated by - - - is a double bond.

2. The method of claim 1, wherein $R_1$ is an amino group ($NH_2$); $R_2$ is hydrogen; and the portion indicated by - - - is a double bond.

3. The method of claim 1, wherein $R_1$ is a dimethylamino group ($N(CH_3)_2$); $R_2$ is a hydroxyl group (OH); and the portion indicated by - - - is a double bond.

4. The method of claim 1, wherein the compound of formula 1 is selected from the group consisting of the following compounds:
   1) 3-[3-(1H-indol-3-yl)acrylamido]benzamide; and
   2) 3-[3-(1H-indol-3-yl)acrylamido]-4-hydroxy-N,N-dimethylbenzamide.

5. The method of claim 1, wherein the pluripotent stem cells are embryonic stem cells or induced pluripotent stem cells.

6. The method of claim 1, wherein the pluripotent stem cells are of human origin.

7. The method of claim 1, wherein the concentration of the compound of formula 1 or a pharmaceutically acceptable salt thereof is 0.01-20 μM.

8. The method of claim 1, culturing pluripotent stem cells in an undifferentiated state corresponds to an increase in Oct4 and H3K9ace level compared to those in a control group not cultured in the composition.

* * * * *

```
                        SEQUENCE LISTING

<160> NUMBER OF SEQ ID NOS: 6

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atttgttttt tgggtagtta aaggt                                             25

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccaactatct tcatcttaat aacatcc                                           27

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggatgttatt aagatgaaga tagttgg                                           27

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cctaaactcc ccttcaaaat ctatt                                             25
```

```
<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tggttaggtt ggttttaaat ttttg                                    25

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aacccaccct tataaattct caatta                                   26
```